United States Patent
Houde et al.

(10) Patent No.: US 10,792,484 B2
(45) Date of Patent: Oct. 6, 2020

(54) VASCULAR ACCESS PORTS AND PROCESSES FOR THEIR MANUFACTURE

(71) Applicant: Praxis Powder Technology, Inc., Queensbury, NY (US)

(72) Inventors: Eric Houde, Queensbury, NY (US); Joseph A. Grohowski, Jr., Glens Falls, NY (US)

(73) Assignee: Praxis Powder Technology, Inc., Queensbury, NY (US)

( * ) Notice: Subject to any disclaimer, the term of this patent is extended or adjusted under 35 U.S.C. 154(b) by 0 days.

(21) Appl. No.: 15/286,934

(22) Filed: Oct. 6, 2016

(65) Prior Publication Data

US 2017/0095654 A1   Apr. 6, 2017

Related U.S. Application Data

(60) Provisional application No. 62/238,031, filed on Oct. 6, 2015.

(51) Int. Cl.
*A61M 39/02* (2006.01)
*A61M 39/00* (2006.01)

(52) U.S. Cl.
CPC . *A61M 39/0208* (2013.01); *A61M 2039/0036* (2013.01); *A61M 2207/00* (2013.01)

(58) Field of Classification Search
CPC ...... A61M 39/0208; A61M 2039/0036; A61M 2207/00
USPC .................................................. 604/288.02
See application file for complete search history.

(56) References Cited

U.S. PATENT DOCUMENTS

| | | | |
|---|---|---|---|
| 5,178,612 A | 1/1993 | Fenton, Jr. | |
| 5,312,337 A | 5/1994 | Flaherty et al. | |
| 5,951,512 A | 9/1999 | Dalton | |
| 6,086,555 A * | 7/2000 | Eliasen | A61M 39/0208 604/175 |
| 8,075,536 B2 * | 12/2011 | Gray | A61M 39/0208 604/288.01 |
| 8,267,915 B2 | 9/2012 | Daly | |
| 8,337,464 B2 | 12/2012 | Young | |
| 8,974,379 B2 * | 3/2015 | Hashiba | A61B 17/3421 600/184 |
| 2005/0171502 A1 * | 8/2005 | Daly | A61M 39/0208 604/502 |
| 2007/0270770 A1 * | 11/2007 | Bizup | A61M 39/0208 604/288.02 |

(Continued)

OTHER PUBLICATIONS

International Search Report, PCT/US2016/055690, dated Dec. 15, 2016.

(Continued)

*Primary Examiner* — Phillip A Gray
(74) *Attorney, Agent, or Firm* — Charney IP Law LLC

(57) ABSTRACT

A vascular access port includes a base with a floor. A cap is engaged with the base to form a reservoir above the floor as a septum seals the reservoir in a fluid-tight manner. An outlet is in fluid communication with the reservoir. At least one of the base and cap is formed by metal injection molding. The cap and base may be engaged with a snap fit connection or a rotatable connection. The fluid communication may be along a non-tangential non-radial flow path. The flow path may be asymmetrical and may also include textured walls.

22 Claims, 21 Drawing Sheets

(56) References Cited

U.S. PATENT DOCUMENTS

2008/0243080 A1* 10/2008 Chang .................. A61M 25/01
604/164.01

OTHER PUBLICATIONS

International Preliminary Report on Patentability, PCT/US2016/055690, dated Apr. 10, 2018.
Written Opinion of the International Searching Authority, PCT/US2016/055690, dated Dec. 15, 2016.

* cited by examiner

VASCULAR ACCESS PORTS AND PROCESSES FOR THEIR MANUFACTURE

CROSS-REFERENCE TO RELATED APPLICATIONS

The present application claims benefit of U.S. Provisional Patent Application Ser. No. 62/238,031, filed Oct. 6, 2015, the disclosure of which is hereby incorporated by reference herein.

BACKGROUND OF THE INVENTION

Vascular access ports are medical devices which are a means of administering fluid to patients directly into their bloodstream. Ports are implanted between the skin and muscle tissue and are typically comprised of an elastomeric septum, a housing with an internal chamber and an exit which connects to a catheter segment. The catheter segment is connected at its other end to a blood vessel.

In applications where the fluid is delivered under pressure it is preferred to use ports constructed of metal and titanium is the preferred metal for these types of products. Conventional metal ports are assembled from machined elements and joined via a press fit and laser welding.

BRIEF SUMMARY OF THE INVENTION

Although well received, the conventional manufacturing methods used to fabricate vascular access ports are costly and limit the design flexibility. Instead, it has been found that metal powder injection molding (MIM) would permit design innovations such as molded metal snap fits (also referred to as snap fit interlocks) as an economical alternative to precision machined press fits. Moreover, the introduction of complex flow paths into ports by the incorporation of sacrificial or soluble (dissolvable) cores in the molded articles is also feasible using MIM technology. Such design innovation can improve the functionality of the device as well as reduce the cost of manufacture.

In accordance with one embodiment, the invention provides for a vascular access port adapted to be implanted subcutaneously, the vascular access port comprising a hollow main port structure forming a reservoir above a floor, a septum sealing the reservoir in a fluid-tight manner, and a port outlet, the port outlet being in fluid communication with the reservoir via a non-tangential non-radial flow path.

In accordance with a second embodiment, the invention provides for a vascular access port adapted to be implanted subcutaneously, the vascular access port comprising a hollow main port structure forming a reservoir above a floor, a septum sealing the reservoir in a fluid-tight manner, and a port outlet, the port outlet being in fluid communication with the reservoir via a non-tangential non-radial flow path, wherein the main port structure comprises a base and a cap, the non-tangential non-radial flow path being formed in the base through the use of a sacrificial insert.

In accordance with a third embodiment, the invention provides for a vascular access port adapted to be implanted subcutaneously, the vascular access port comprising a hollow main port structure forming a reservoir above a floor, a septum sealing the reservoir in a fluid-tight manner, and a port outlet, the port outlet being in fluid communication with the reservoir via a non-tangential non-radial flow path, wherein the main port structure comprises a base and a cap, the base and the cap being coupled by at least one linearly engaging snap fit connection.

In accordance with a fourth embodiment, the invention provides for a vascular access port adapted to be implanted subcutaneously, the vascular access port comprising a hollow main port structure forming a reservoir above a floor, a septum sealing the reservoir in a fluid-tight manner, and a port outlet, the port outlet being in fluid communication with the reservoir via a non-tangential non-radial flow path, wherein the main port structure comprises a base and a cap, the base and the cap being coupled by at least one linearly engaging snap fit connection, wherein the linearly engaging snap fit connection is engaged by relative linear movement of the cap toward the base, at least one of the base and the cap including a portion which resiliently deflects in a direction perpendicular to the relative linear movement via physical interference to secure the at least one linearly engaging snap fit connection.

In accordance with a fifth embodiment, the invention provides for a vascular access port adapted to be implanted subcutaneously, the vascular access port comprising a hollow main port structure forming a reservoir above a floor, a septum sealing the reservoir in a fluid-tight manner, and a port outlet, the port outlet being in fluid communication with the reservoir via a non-tangential non-radial flow path, wherein the main port structure comprises a base and a cap, the base and the cap being coupled by rotational engagement.

In accordance with a sixth embodiment, the invention provides for a vascular access port adapted to be implanted subcutaneously, the vascular access port comprising a hollow main port structure forming a reservoir above a floor, a septum sealing the reservoir in a fluid-tight manner, and a port outlet, the port outlet being in fluid communication with the reservoir via a non-tangential non-radial flow path, wherein the floor slopes downward toward the non-tangential non-radial flow path.

In accordance with a seventh embodiment, the invention provides for a vascular access port adapted to be implanted subcutaneously, the vascular access port comprising a hollow main port structure forming a reservoir above a floor, a septum sealing the reservoir in a fluid-tight manner, and a port outlet, the port outlet being in fluid communication with the reservoir via a non-tangential non-radial flow path, wherein the non-tangential non-radial flow path is configured to create turbulent flow in fluid flowing from the reservoir to the outlet.

In accordance with an eighth embodiment, the invention provides for a vascular access port adapted to be implanted subcutaneously, the vascular access port comprising a hollow main port structure forming a reservoir above a floor, a septum sealing the reservoir in a fluid-tight manner, and a port outlet, the port outlet being in fluid communication with the reservoir via a non-tangential non-radial flow path, wherein the non-tangential non-radial flow path includes a textured wall.

In accordance with a ninth embodiment, the invention provides for a vascular access port adapted to be implanted subcutaneously, the vascular access port comprising a hollow main port structure forming a reservoir above a floor, a septum sealing the reservoir in a fluid-tight manner, and a port outlet, the port outlet being in fluid communication with the reservoir via a non-tangential non-radial flow path, wherein the non-tangential non-radial flow path has a cross-sectional area that varies along its length.

In accordance with a tenth embodiment, the invention provides for a vascular access port adapted to be implanted subcutaneously, the vascular access port comprising, a base with a floor, a cap engaged with the base to form a reservoir above the floor, a septum sealing the reservoir in a fluid-tight manner, and an outlet, the outlet being in fluid communication with the reservoir, wherein at least one of the base and the cap are formed by metal injection molding.

In accordance with an eleventh embodiment, the invention provides for a vascular access port adapted to be implanted subcutaneously, the vascular access port comprising, a base with a floor, a cap engaged with the base to form a reservoir above the floor, a septum sealing the reservoir in a fluid-tight manner, and an outlet, the outlet being in fluid communication with the reservoir, wherein at least one of the base and the cap are formed by metal injection molding, wherein the base and the cap are coupled by at least one linearly engaging snap fit connection.

In accordance with a twelfth embodiment, the invention provides for a vascular access port adapted to be implanted subcutaneously, the vascular access port comprising, a base with a floor, a cap engaged with the base to form a reservoir above the floor, a septum sealing the reservoir in a fluid-tight manner, and an outlet, the outlet being in fluid communication with the reservoir, wherein at least one of the base and the cap are formed by metal injection molding, wherein the base and the cap are coupled by at least one linearly engaging snap fit connection and wherein the at least one linearly engaging snap fit connection is engaged by relative linear movement of the cap toward the base, at least one of the base and the cap including portions which resiliently deflect in a direction perpendicular to the relative linear movement via physical interference to couple the base and the cap.

In accordance with a thirteenth embodiment, the invention provides for a vascular access port adapted to be implanted subcutaneously, the vascular access port comprising, a base with a floor, a cap engaged with the base to form a reservoir above the floor, a septum sealing the reservoir in a fluid-tight manner, and an outlet, the outlet being in fluid communication with the reservoir, wherein at least one of the base and the cap are formed by metal injection molding, wherein the cap and the base are engaged through rotation of the cap relative to the base.

In accordance with a fourteenth embodiment, the invention provides for a vascular access port adapted to be implanted subcutaneously, the vascular access port comprising, a base with a floor, a cap engaged with the base to form a reservoir above the floor, a septum sealing the reservoir in a fluid-tight manner, and an outlet, the outlet being in fluid communication with the reservoir, wherein at least one of the base and the cap are formed by metal injection molding, wherein the cap and the base are engaged through rotation of the cap relative to the base and wherein fluid communication between the reservoir and the outlet is through a stem, the stem being adapted to limit rotation of the cap relative to the base.

In accordance with a fifteenth embodiment, the invention provides for a vascular access port adapted to be implanted subcutaneously, the vascular access port comprising, a base with a floor, a cap engaged with the base to form a reservoir above the floor, a septum sealing the reservoir in a fluid-tight manner, and an outlet, the outlet being in fluid communication with the reservoir, wherein at least one of the base and the cap are formed by metal injection molding, the port further comprising an asymmetrical fluid flow path between the reservoir and the outlet.

In accordance with a sixteenth embodiment, the invention provides for a method of providing a vascular access port suitable for subcutaneous implant, the method comprising providing a base with a floor, providing a cap, fitting a septum between the base and the cap and engaging the cap with the base to form a reservoir above the floor, the reservoir being sealed in a fluid-tight manner by the septum, wherein the engaged cap and base include a fluid flow path from the reservoir to an outlet and wherein the engaging is achieved either through at least one linear snap fit connection or a rotational connection.

In accordance with a seventeenth embodiment, the invention provides for a method of providing a vascular access port suitable for subcutaneous implant, the method comprising providing a base with a floor, providing a cap, fitting a septum between the base and the cap and engaging the cap with the base to form a reservoir above the floor, the reservoir being sealed in a fluid-tight manner by the septum, wherein the engaged cap and base include a fluid flow path from the reservoir to an outlet and wherein the engaging is achieved either through at least one linear snap fit connection or a rotational connection, wherein engagement of the cap and the base is through at least one linear snap fit connection, the at least one linear snap fit connection resiliently deflecting portions of at least one of the cap and the base in a direction perpendicular to relative linear movement of the cap and base via physical interference to engage the cap and base.

In accordance with an eighteenth embodiment, the invention provides for a method of providing a vascular access port suitable for subcutaneous implant, the method comprising providing a base with a floor, providing a cap, fitting a septum between the base and the cap and engaging the cap with the base to form a reservoir above the floor, the reservoir being sealed in a fluid-tight manner by the septum, wherein the engaged cap and base include a fluid flow path from the reservoir to an outlet and wherein the engaging is achieved either through at least one linear snap fit connection or a rotational connection, wherein engagement of the cap and the base is through rotation of the cap relative to the base, the method further comprising placing a thrust washer adjacent to the septum.

In accordance with a nineteenth embodiment, the invention provides for a method of providing a vascular access port suitable for subcutaneous implant, the method comprising providing a base with a floor, providing a cap, fitting a septum between the base and the cap and engaging the cap with the base to form a reservoir above the floor, the reservoir being sealed in a fluid-tight manner by the septum, wherein the engaged cap and base include a fluid flow path from the reservoir to an outlet and wherein the engaging is achieved either through at least one linear snap fit connection or a rotational connection, wherein engagement of the cap and the base is through rotation of the cap relative to the base, and wherein rotation of the cap relative to the base causes a helix in the septum.

In accordance with a twentieth embodiment, the invention provides for a method of providing a vascular access port suitable for subcutaneous implant, the method comprising providing a base with a floor, providing a cap, fitting a septum between the base and the cap and engaging the cap with the base to form a reservoir above the floor, the reservoir being sealed in a fluid-tight manner by the septum, wherein the engaged cap and base include a fluid flow path from the reservoir to an outlet and wherein the engaging is achieved either through at least one linear snap fit connection or a rotational connection, wherein the fluid flow path is asymmetrical.

Other embodiments of the invention will be realized upon review of the detailed description provided below.

BRIEF DESCRIPTION OF THE DRAWINGS

The subject matter regarded as the invention is particularly pointed out and distinctly claimed in the concluding portion of the specification. The invention, however, both as to organization and method of operation, together with features, objects, and advantages thereof, will be or become apparent to one with skill in the art upon reference to the following detailed description when read with the accompanying drawings. It is intended that any additional organizations, methods of operation, features, objects or advantages ascertained by one skilled in the art be included within this description, be within the scope of the present invention, and be protected by the accompanying claims.

With respect to the drawings.

DETAILED DESCRIPTION

Figure 1:
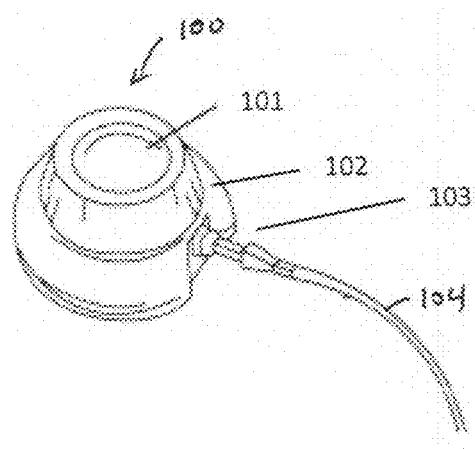
FIG. 1 shows a conventional single lumen vascular access port.

In the following are described the preferred embodiments of the VASCULAR ACCESS PORTS AND PROCESSES FOR THEIR MANUFACTURE in accordance with the present invention. In describing the embodiments illustrated in the drawings, specific terminology will be used for the sake of clarity. However, the invention is not intended to be limited to the specific terms so selected, and it is to be understood that each specific term includes all technical equivalents that operate in a similar manner to accomplish a similar purpose. Where like elements have been depicted in multiple embodiments, identical reference numerals have been used in the multiple embodiments for ease of understanding.

Throughout this disclosure reference is made to metal injection molding ("MIM"), and parts formed through MIM. It is to be understood that the phrase metal injection molding refers specifically to powder metal injection molding. The powder metal may be selected from a wide range of known biocompatible metals, including titanium and stainless steel. In preferred embodiments of the invention, either commercially pure titanium or titanium alloy powders, such as Ti-6Al-4V alloy powders, are used. Methods of metal injection molding, including selection and use of binders and subsequent sintering, are well known in the field of biocompatible implantable devices.

Reference is also made to sacrificial or soluble (dissolvable) cores or inserts. These cores can be used in the MIM process to create complex features such as undercuts, internal cavities, hollow areas, voids, flow channels, bumps, ridges, etc.

The sacrificial inserts can be removed after molding by dissolution or decomposition. The material should be readily removable from the injection molded article without leaving behind residual material that could contaminate the molded article. This can be achieved primarily by dissolving the insert or thermally decomposing the insert. In a preferred embodiment, the insert is removed before thermal debinding. Liquid may be used to extract the first phase of the MIM binder prior to thermal debinding. This liquid can be water or a solvent and ideally the insert material can be chosen to be removed using the same solvent. Removing the insert prior to thermal debinding ensures that the insert does not contaminate the finished article. Some MIM systems use a first phase that is catalytically decomposed at low temperature; the insert material can be selected to be compatible with this type of process as well.

According to the invention, the material used for the insert should withstand the temperature and pressure of the molten metal injection molding feedstock. Many polymer materials can be used as an insert material as known in the art. Preferred embodiment materials are acrylonitrile butadiene styrene ("ABS"), ABS-like materials, and styrene and acrylic materials and other materials having similar thermal and solubility characteristics.

Suitable inserts may also be formed through additive manufacturing ("AM") processes. Materials such as cellulose based resins are good candidates for AM inserts because they readily satisfy the requirement of withstanding temperature and pressure of injection molding, yet can be selected to be readily soluble in water or organic solvents. Material blends such as a metal salt with a binder can be manufactured by AM as inserts.

It is also noted that various components may be described as being "fluidly connected" or in "fluid communication" in relation to each other and/or a fluid flow path. Where such terminology is used, it is to be understood in accordance with its broadest reasonable interpretation to include direct physical connections between the identified components, or connections through additional intervening components, so long as fluid may flow from one component to the other in the manner prescribed.

Vascular access ports are medical devices which provide a means of administering fluid to a patient's vascular system. Ports are implanted between the skin and muscle tissue and are comprised a housing with an internal chamber with an exit which connects to a catheter. The chamber is sealed with an elastomeric septum. The catheter segment is connected to a blood vessel of the vascular system.

FIG. 1 shows a conventional single lumen port 100 having an elastomeric septum 101 sealing a hollow housing forming a reservoir 102. A port outlet 103 connect to a catheter 104 such that the catheter is in fluid communication with the reservoir 102.

Figure 2:
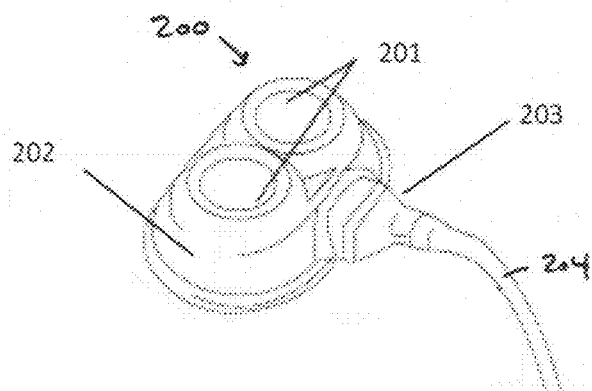
FIG. 2 shows a conventional dual lumen vascular access port.

As further conventional example, FIG. 2 shows a dual lumen port 200 having two elastomeric septa 201 sealing a hollow housing reservoir 202 with outlets 203 that connect to catheter 204. In this example there is a single catheter 204 connected to both hollow housings 202. In other examples, there may be one catheter associated with each hollow housing to keep the fluids separated.

Fluid communication is partially established via a special needle called a non-coring needle or Huber needle. The needle is attached to a fluid delivery device (syringe, pump, etc) and fluids, such as medications, dietary supplements, and the like, are injected through the needle, into the port housing chamber via penetration of the elastomeric septum. The fluids then pass through a flow path formed in the port, then the port outlet and catheter, into the blood vessel to which the catheter is attached.

Figure 3:
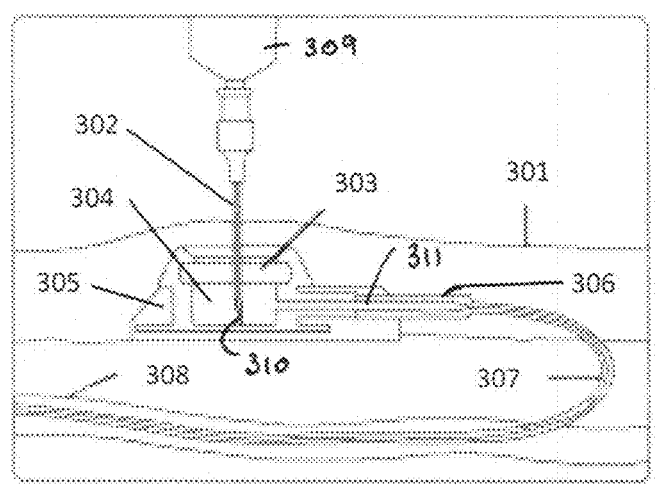
FIG. 3 is a schematic of a conventional vascular access port as implanted.

FIG. 3 illustrates a conventional port 300 as implanted under the skin 301. The needle 302 is specially designed to puncture through the septum 303 without creating a permanent hole. The exit 310 of the needle 302, after puncturing through the septum 303, resides in a reservoir 304 within the hollow port housing 305. Fluid introduced into the reservoir 304 exits through a flow path 311 and then a stem with outlet 306 and catheter 307, and is delivered to the blood vessel 308. The needle is attached to a fluid delivery device (syringe, pump, etc) 309 and fluids are injected through the needle, into the port housing reservoir 304, through the flow path 311 and port outlet 306, and catheter 307, and finally out into the blood vessel 308.

Ports may be fabricated out of metal or plastic depending on physician and patient needs. Metal ports are preferred for their ability to withstand damage from needles and are their general durability while plastic ports have the benefit of casting no x-ray shadows. On the whole, demand for metal ports has been increasing. Titanium and its alloys are the preferred metal material for the construction of ports because of titanium's high biocompatibility, low density, and non-magnetic nature.

Metal ports historically have used a press fit to join the upper and lower portions of the housing. This press fit serves the dual function of joining the housing and securing and compressing the septum in the housing. Holding the septum in compression helps to improve its performance with respect to sealing.

Figure 4:
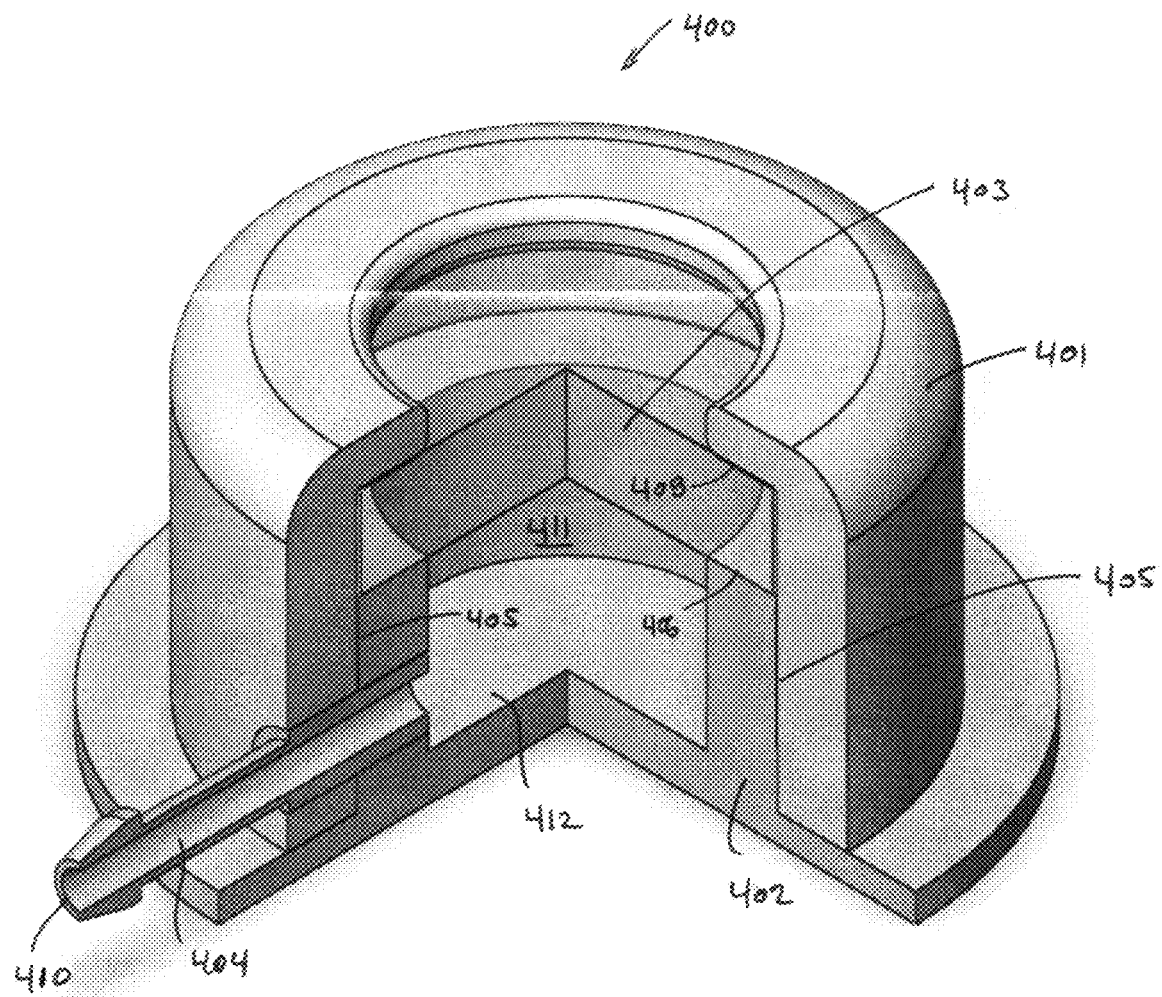
FIG. 4 shows a partial sectional view of a vascular access port of conventional construction with a press fit connection below the stem.

FIG. 4 depicts a typical construction of a single lumen port 400 having a press fit below the stem. Ports 400 such as this one are comprised of a housing assembly which has an upper portion 401 and lower portion 402 which partially overlap to capture and secure the septum 403, the septum resting on an upper ledge 406 of the lower portion and being trapped by an overhang 408 of the upper portion to form a reservoir 411 above the floor 412 in the hollow port 400. The upper portion 401 may also be referred to as the cap and the lower portion 402 may also be referred to as the base. A straight component, often referred to as a stem 404, extends radially from the housing, creating the fluid outlet 410 of the port. This component is also typically the connection point between the catheter and the housing assembly. The typical means of assembly between the upper and lower segments which capture the septum is a press fit 405 (also referred to as a friction fit or interference fit). In FIG. 4, the press fit 405 is in the same area as the stem 404, and forms a surface with high friction connection.

Figure 5:
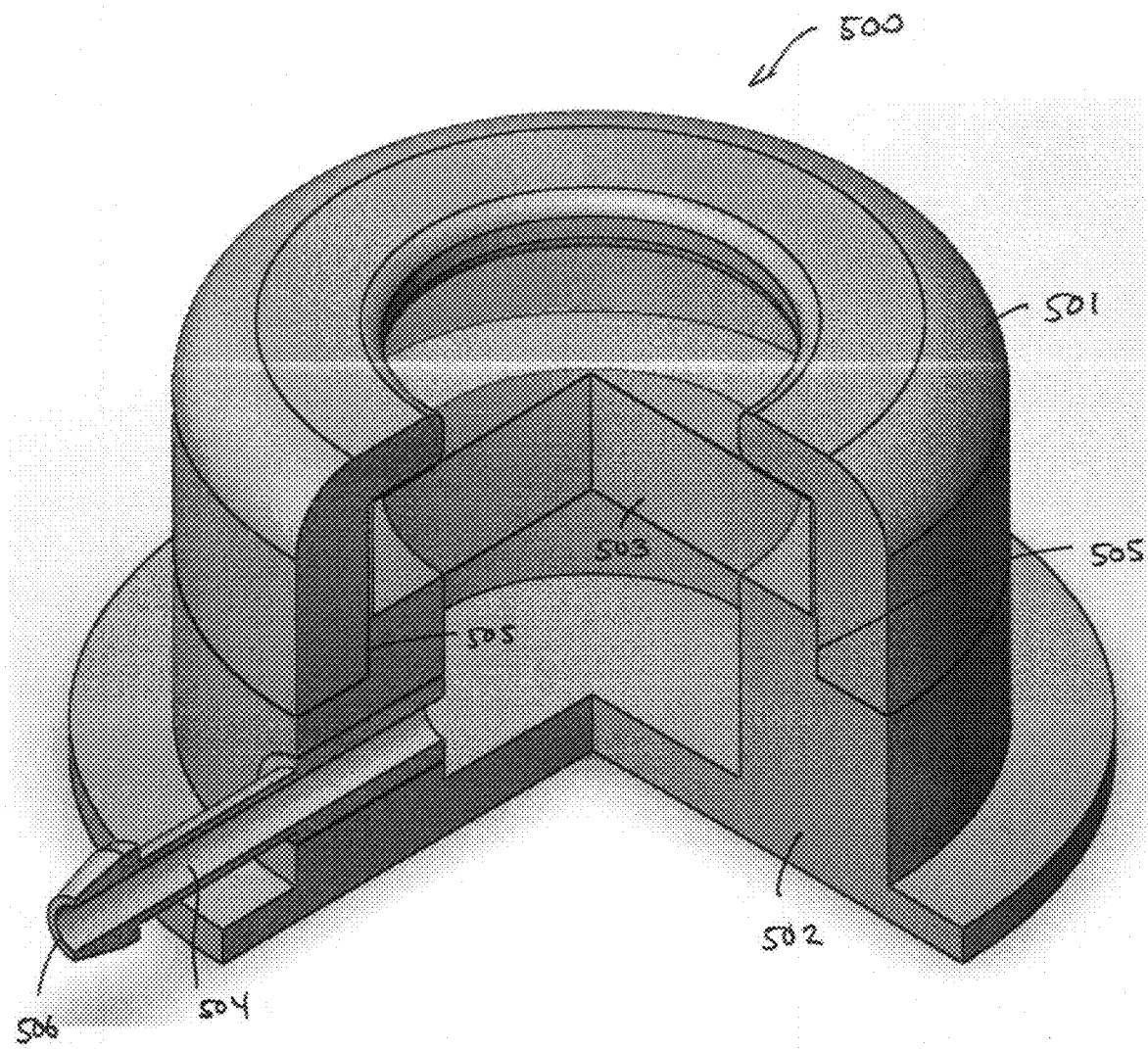
FIG. 5 shows a partial sectional view of a vascular access port of conventional construction with a press fit connection above the stem.

Alternatively, the press fit surface may be above the stem. FIG. 5 depicts a typical construction of a single lumen port 500 having such a configuration. This port 500 has an upper portion 501 and lower portion 502 which capture and secure the septum 503. The stem 504 extends radially from the housing creating the fluid outlet 506 of the port. Above the stem 504 is the press fit 505 between the upper portion 501 and lower portion 502.

Press fit parts require deformation of one or more of the components to achieve connection characteristics suitable for a vascular access port and a high degree of accuracy in part tolerances is required. For this reason, the mating surfaces of press fit parts are generally machined. For example, for the port 400, the outer surface of the lower portion 402 and the inner surface of the upper portion 401 would be machined along the press fit surface 405 so they can be press fit in an arrangement where either or both the lower portion and upper portion deform appropriately during pressing.

A maximum allowance of 0.0025 inch (0.25%) per inch of diameter is typical for press fit parts. Thus, a port with two parts having nominal 1-inch diameters mush be machined to tolerances of between 0.99875 inch and 1.00125 inch. In this manner, an outer diameter of no greater than 1.00125 inch will properly press fit with an inner diameter of no less than 0.99875 inch.

Metal injection molding can theoretically be used to form certain port geometries; however, it is challenging to produce parts with enough precision to provide for a proper press fit. Of note, titanium metal injection molded parts of approximately 1-inch in diameter can typically be manufactured to tolerances of only +/−0.006 inch. For conventional vascular access ports, this is not a tight enough tolerance and the press fit parts must be machined. The procedures of this invention provides MIM snap fit elements that would replace the press fit and allow for the net shape production of these geometries via MIM, even without the need for subsequent machining. Metal snap fits also allow more positive and robust joining of the upper and lower portion as well as rotational connections in addition to the typical linear connection.

Snap fit elements provide other benefits over press fit connections in that snap fit elements can perform the dual function of joining the upper and lower portion and rotationally locating them with respect to one another.

Figure 6:
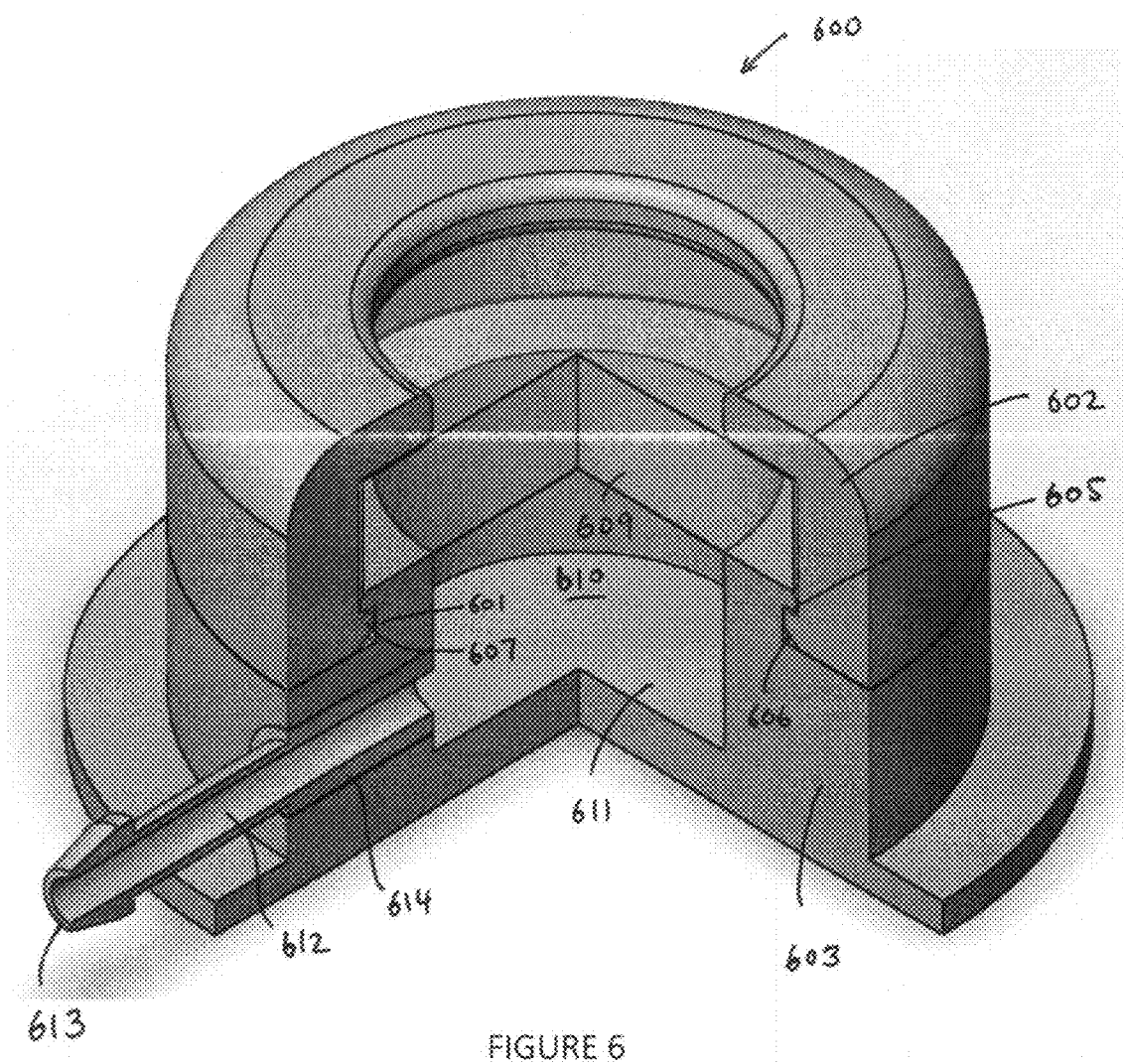
FIG. 6 shows a partial sectional view of a vascular access port with a snap fit connection internal to the upper housing.

FIG. 6 depicts a partially cut-away perspective view of a port housing 600 having a continuous snap fit interlock 601 connecting an upper housing 602 to a lower housing 603. While the exact geometry may vary, the port housing 600 is generally circular with a base 608 being of a larger diameter than the upper housing 602 and mating portion of the lower housing 603. The interlock 601 is achieved by creating, through a sacrificial or soluble core, an internal ledge 605 in the upper housing 602 along with a recessed area 606 to accept a bead 607 formed, again through the use of a sacrificial or soluble core, in the lower housing 603. The housings 602, 603 flex radially during assembly, as the upper housing 602 and lower housing 603 are brought together by respective linear movement, and portions of one or both deflect by interference until the snap fitting 601 has reached its final non-stressed snap fit location and the components are permitted to resiliently return to their natural conditions, as shown in FIG. 6. This process also locks a septum 609 between the upper housing 602 and lower housing 603. It will be appreciated that the upper and lower housings 602, 603 form a reservoir 610 beneath the septum 609 and above a floor 611 of the lower housing.

Extending through the lower housing 603 and into the reservoir 610 is a stem 612 having an outlet 613. The stem 612 serves to permit fluid introduced through the septum 609 and into the reservoir 610 to flow out of the port 600. Although not shown, the outlet 613 may be connected to a catheter which in turn may be inserted into the vascular system of a port patient to administer the fluid. The interface 614 between the stem 612 and lower housing 603 may be made fluid-tight by virtue of being press fit, laser welded, press fit with an O-ring, or through other known techniques. In this configuration, the cross-section of the stem 612 is circular and the fluid flow path through the stem is linear. In later configurations the cross-section may be other than circular and/or may vary in cross-sectional area so as to be asymmetrical.

The snap fit 601 depicted in FIG. 6 is external to the lower housing 603, i.e. where the bead 607 is on the outside of the housing. In other embodiments, the snap fit interlock 601 may be internal to a lower housing, for example as will be seen in FIG. 7.

Figure 8:
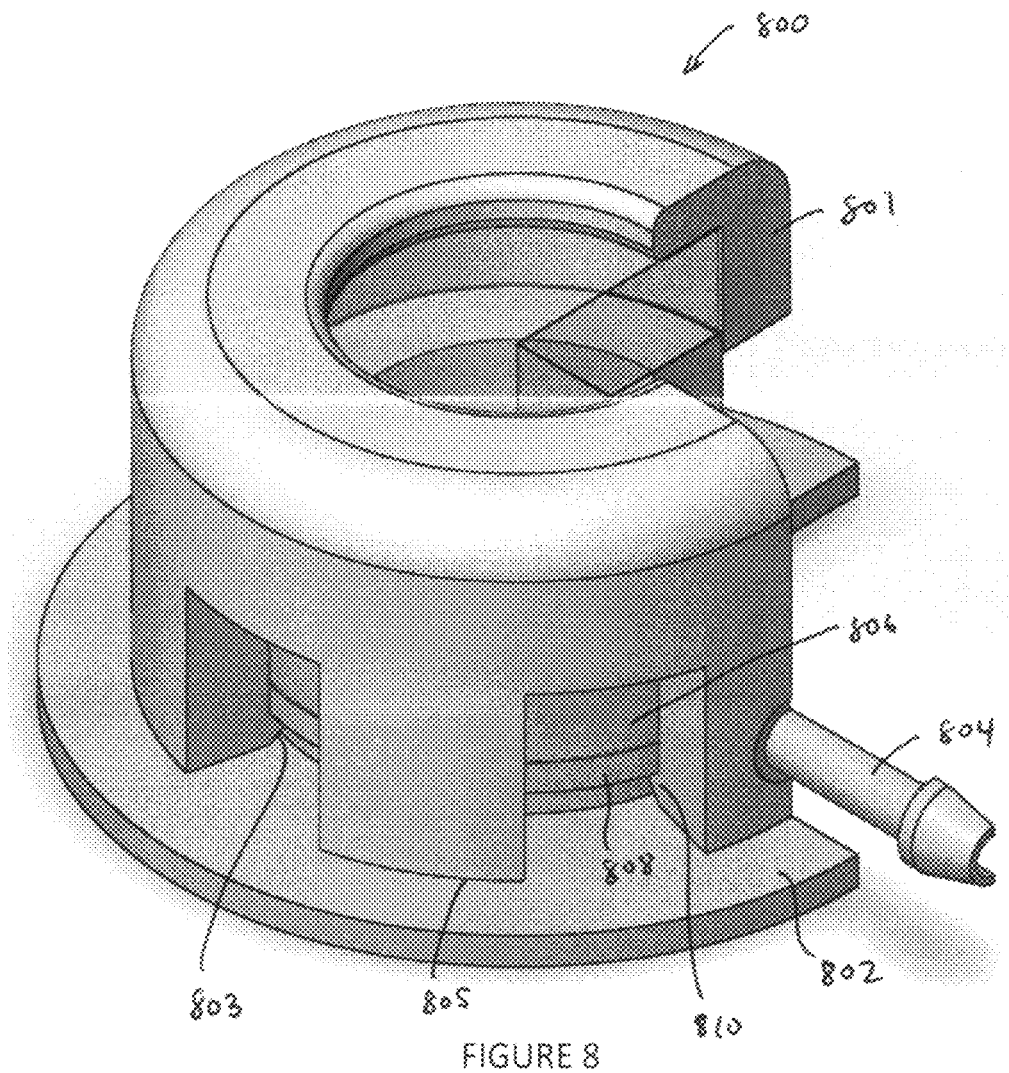
FIG. 8 shows a partial sectional view of a vascular access port with a segmented annular snap fit connection.
Figure 9:
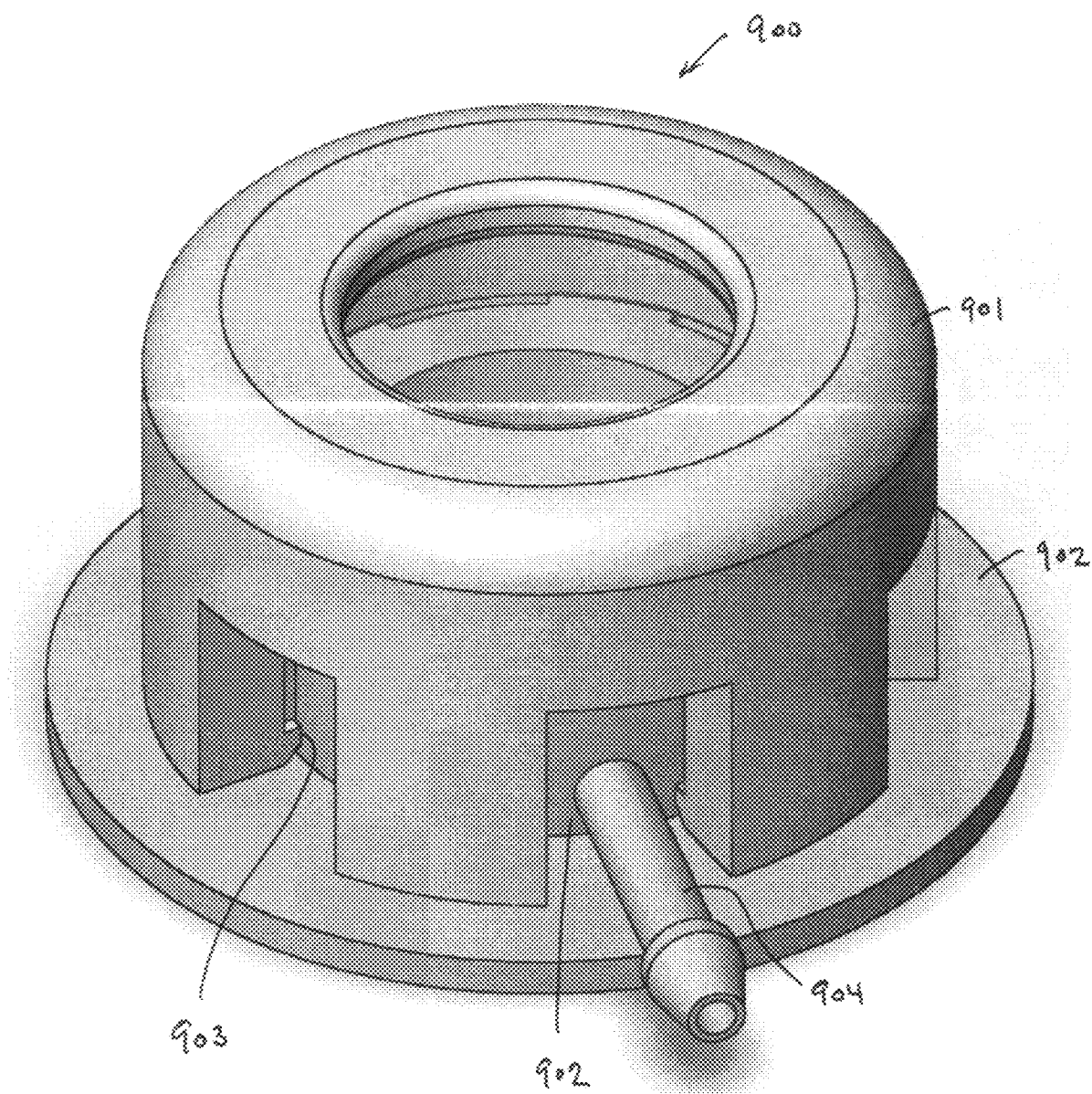
FIG. 9 shows a vascular access port with a segmented annular snap fit connection and integral stem.

Moreover, the snap fit 601 of FIG. 6 is continuous around the entire 360-degree circumference of the housings 602, 603. In other embodiments, such as shown in FIGS. 8 and 9, the snap fit may be segmented or discontinuous. In preferred embodiments the snap fit is discontinuous as it has been found that a discontinuous snap fit provides the necessary connective function while requiring less effort to connect the upper and lower housings. Additionally, less material is required for port construction.

Figure 7:
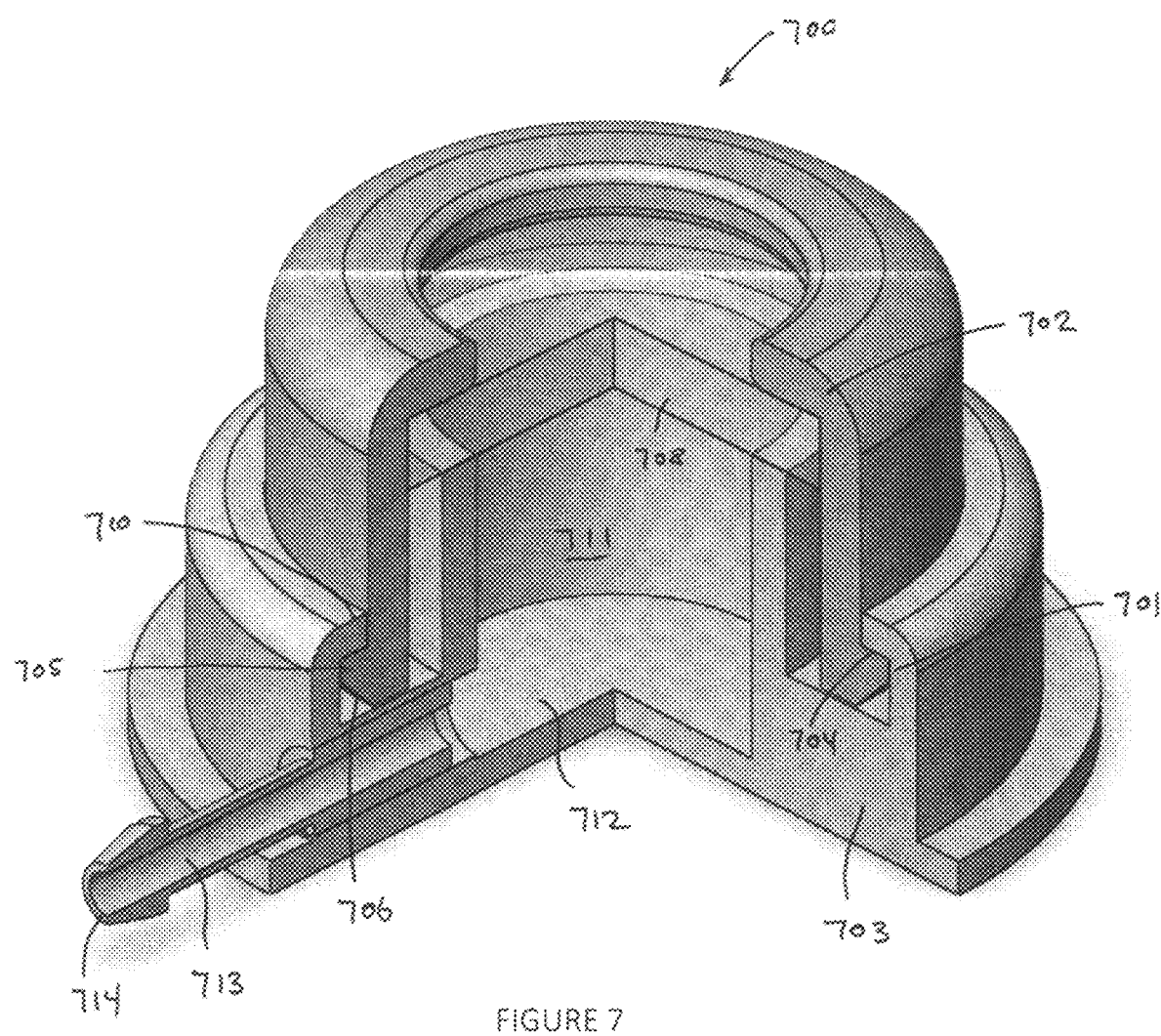
FIG. 7 shows a partial sectional view of a vascular access port with a snap fit connection internal to the lower housing.

FIG. 7 depicts an arrangement providing for a continuous snap fit that is internal to the lower housing of a port 700. The snap fit can also inverted to be internal to the upper housing if so desired. It will be appreciated that the complex features of the port 700 discussed below may be formed through the use of sacrificial or soluble cores.

The port 700 shown in FIG. 7 has a snap fit interlock 701 between the upper housing 702 and the lower housing 703. The snap fit interlock is achieved by creating an internal undercut 704 in the lower housing 703 along with an external bead 705 formed in the upper housing. The bead 705, may include a ramped or tapered portion 706 to aid in the bead fitting over the edge 710 of the lower housing 703 above the internal undercut 704. It will be appreciated that as the upper housing 702 is moved linearly with respect to the lower housing 703, either or both of the bead 705 (and adjacent portions of the upper housing) and the internal undercut 704 (and adjacent portions of the lower housing including the edge 710) will deflect by interference to allow the bead to pass beyond the undercut. Once the bead 705 entirely passes the undercut 704, the deflected portions of the port 700 resiliently return to their natural positions thereby locking the upper housing 702 and lower housing 703 together. This also serves to secure the septum 708 between the upper and lower housings 702, 703 to form a reservoir 711 above the lower housing floor 712. As in the port of FIG. 6, a stem 713 extends from the reservoir 711 to an outlet 714.

Snap fits as depicted in FIGS. 6 and 7 are fully continuous annular snap fits. FIG. 8 illustrates one configuration of a port 800 in which the upper housing 801 is secured to the lower housing 802 via a segmented annular snap fit 803. Segmentation commonly takes the form of sequential slots 806 whereby matching portions of the continuous bead and undercut, such as shown in FIG. 6, are not provided. In the embodiment shown in FIG. 8, the bead 808 of the lower housing 802 is continuous while the undercut 810 of the upper housing 801 is discontinuous. Commonly, 25%-75% of the snap fit surface area may be removed, leaving behind a series of snap fit connections around the perimeter of the device. Further the snap fitting elements do not need to be arranged in an annular fashion. Snap fit elements having flat sections as opposed to curved sections can be employed to reduce the force needed to close the snap fit. It will be appreciated that the depth of the segmented sections are exaggerated in the drawing for clarity of depiction.

FIG. 9 depicts a configuration of a port 900 in which the upper housing 901 is secured to the lower housing 902 via a segmented annular snap fit 903. The port 900 also has an integral stem 904 which is molded simultaneously with the lower housing 902. This may be achieved through the use of sacrificial or soluble cores. Referring back to port 800 of FIG. 8, one will appreciate that the stem 804 is a separate element that is fitted into the port 800 by press fit, laser welding, press fit with an O-ring, or through other known techniques. As shown in FIG. 8, stem 804 also penetrates both the upper housing 801 and lower housing 802 whereas stem 904 of port 900 only penetrates (or is formed integrally with) lower housing 902.

Segmented snaps allow for easier snap fitting while reducing the force required to snap parts together compared to a full annular snap fit as the total affected surface area is lessened. The snap fit element may be visible from the outside of the device as in FIG. 8 or can be incorporated into the device in such a manner that they are not visible from the outside. Using the port 800 of FIG. 8 as an example, the upper housing 801 may extend down to the base 805 of the lower housing 802 to hide the snap fit 803.

Moreover, segmentation can vary with number of segments, size of segments, as well as the thickness of the walls, all in accordance with engineering requirements and ease of installation while in the surgical arena. For example, in stress areas such as near the stem the snap fit connections may be more extensive and represent a larger area in relation to other portions of the port that can hold tight with less local snap fit length.

Figure 10A:
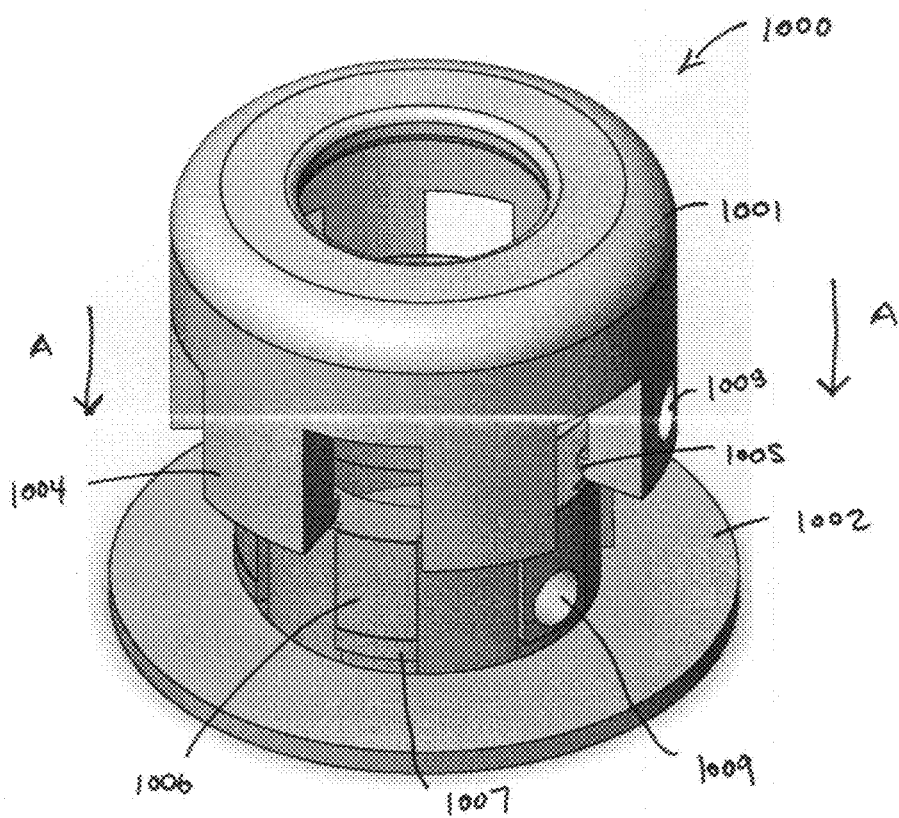
FIGS. 10A through 10D show the assembly sequence of a port with a rotational interlock connection.

In other embodiments of the snap fit, the fit can be achieved via a rotational engagement versus axial stretching of arms over the mating component. FIGS. 10A thorough 10D illustrate a sequential assembly sequence of a port 1000 comprising a cap 1001 and a base 1002. The assembly sequence consists of the cap 1001 being aligned properly and pushed down vertically along arrows A over the base 1002 and then the cap being rotated about the base to interlock the undercut portions of the cap and base. A stem 1003 may be inserted to preserve rotational alignment of the assembly in step 1005.

Figure 10B:
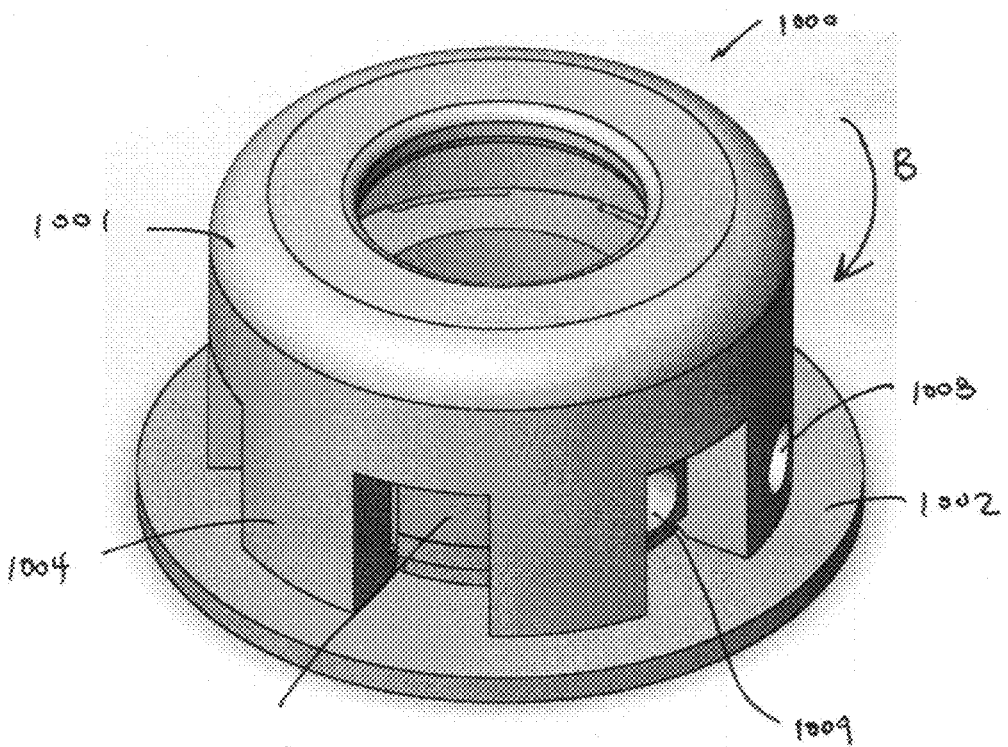
Figure 10C:
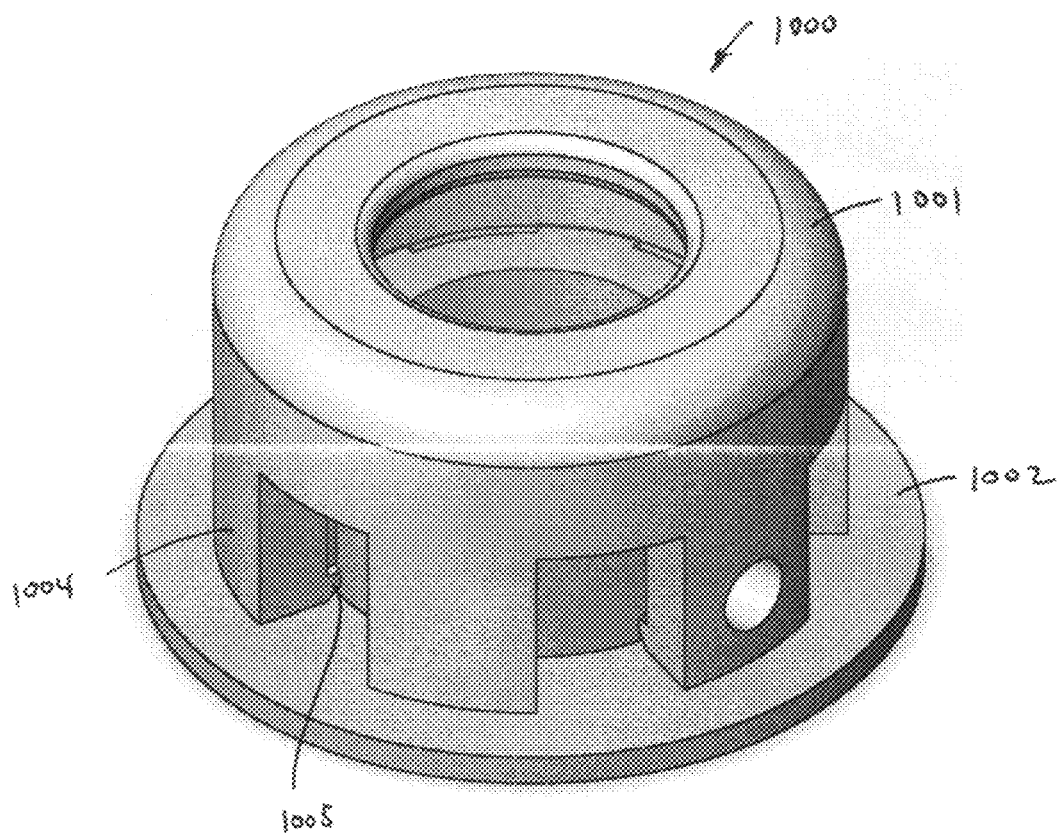
Figure 10D:
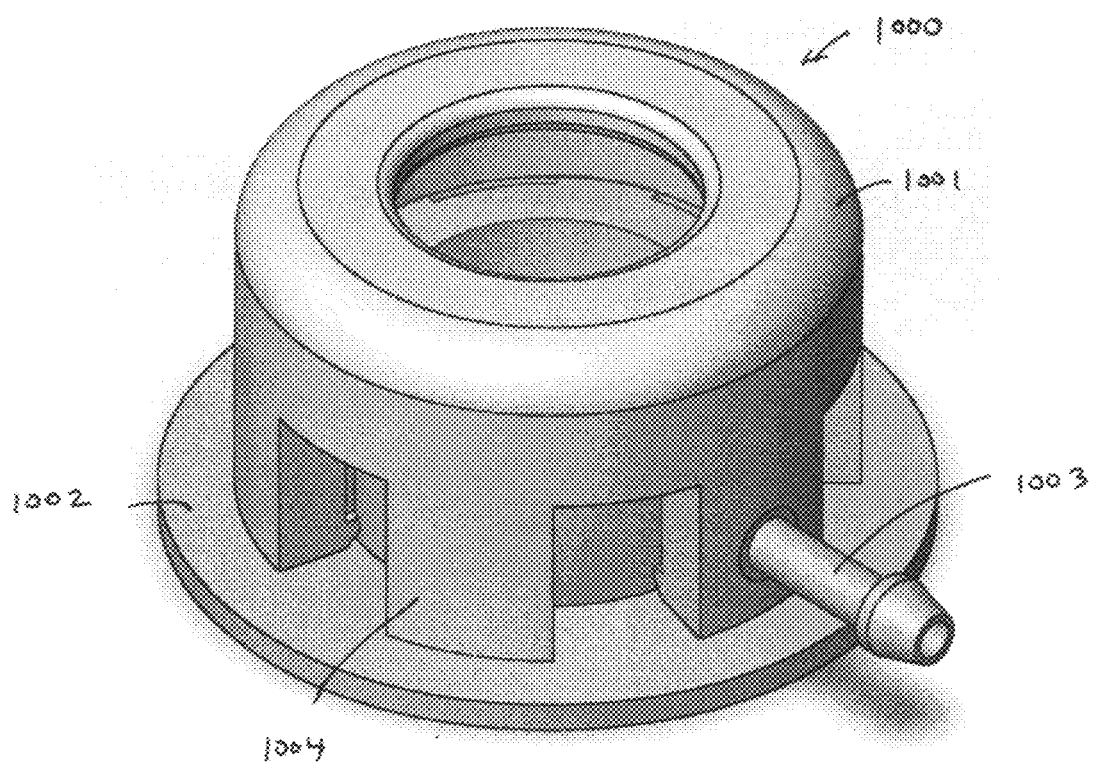

More specifically, the cap 1001 is positioned about the base 1002, as shown in FIG. 10A, such that extension members 1004, containing internal undercuts 1005, are adjacent to protrusions 1006 of the base, where the protrusions form undercuts 1007. This represents the proper alignment previously mentioned. The cap 1001 is then brought downward vertically along arrows A with respect to the base 1002 to the position shown in FIG. 10B. The cap 1001 is then rotated relative to the base 1002 over an engagement area along arrow B to the position shown in FIG. 10C, where the undercuts 1005 of the extension members 1004 mate with the undercuts 1007 of the protrusions 1006 (the undercuts and protrusions being hidden in FIG. 10C) to interlock the cap and the base together. Finally, a stem 1003 is inserted into dual apertures 1008, 1009 formed through the cap 1001 and base 1002, respectively, which align upon the previously discussed rotation. As in other embodiments, the stem 1003 may be affixed via known means.

The amount of rotation required to engage the cap 1001 and base 1002 may be controlled by the amount of contact area of the engagement area.

It will be appreciated that although not shown, the port 1000 of FIGS. 10A through 10D includes a septum placed between the cap 1001 and base 1002. The rotational relationship between the cap 1001 and base 1002 can create a potentially desired torque or twist on the septum to enhance performance of the needle sealing. If torsion of the septum is not desired, then a thrust washer (also not shown) can be placed between septum and cap and/or the septum and base. This thrust washer, or washers, can take form as a simple polyoxymethylene (Acetal) disk or disks.

Figure 11A:
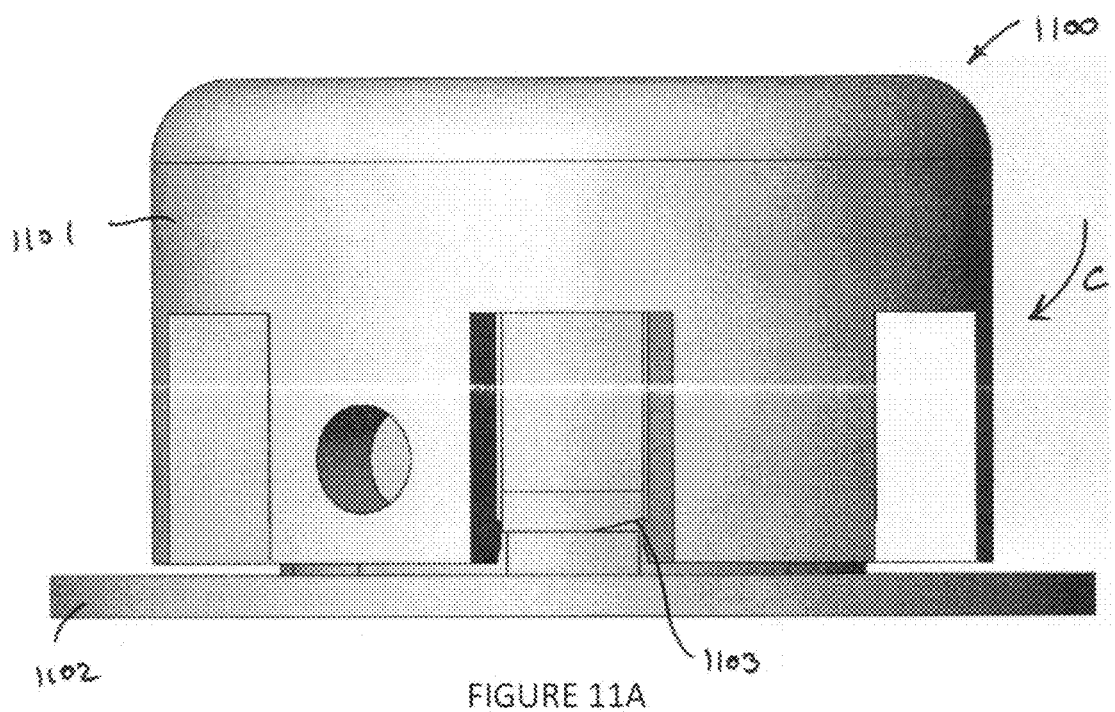
FIGS. 11A and 11B show the assembly sequence of a port with a ramped rotational interlock, FIG. 11B depicting a larger scale view of a portion of the port shown in FIG. 11A.
Figure 11B:
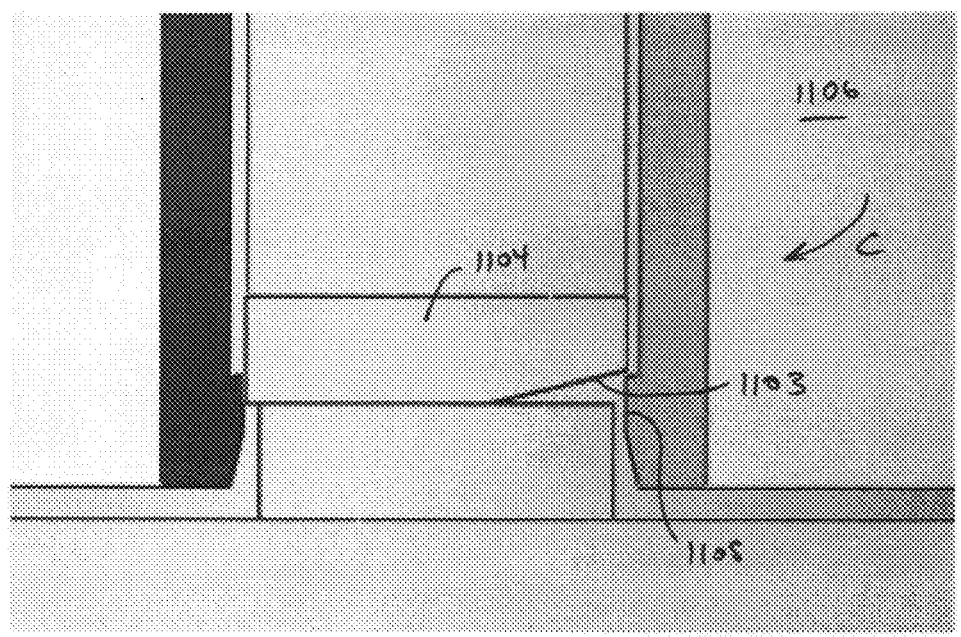

In addition, there are further embodiments to enhance the assembly of the upper and lower housings in rotational engagement. FIGS. 11A and 11B depict a port 1100 having a cap 1101 and a base 1102 that incorporate a ramp 1103 formed in the undercut 1104 of the base to increase the rotational fit of the cap and base as the undercut 1105 of the extension member 1106 slides over the ramp. A ramp 1103 allows for torsional advantage to twist the components together and creates compression via rotational motion. Again, this embodiment may include an advantageous septum twist or thrust washers to prevent septum twist. Of note, the cap 1101 of FIGS. 11A and 11B would rotate clockwise along arrow C to take advantage of the ramp 1103. It will be appreciated that other arrangements may utilize counter-clockwise rotation.

Additionally, a feature such as a detent can be added to prevent the upper and lower housings from untwisting and becoming separated. This can replace need for the stem to act as locking mechanism as in FIGS. 10A through 10D. There are many variations on this assembly design, combining a rotational thread-like element to create compression with a detent function can reduce assembly cost. The detent function can occur as a single snap fit function or a ratchet like element and it can be oriented in the rotational direction of closure as opposed to the axial direction of closure.

Figure 10E:
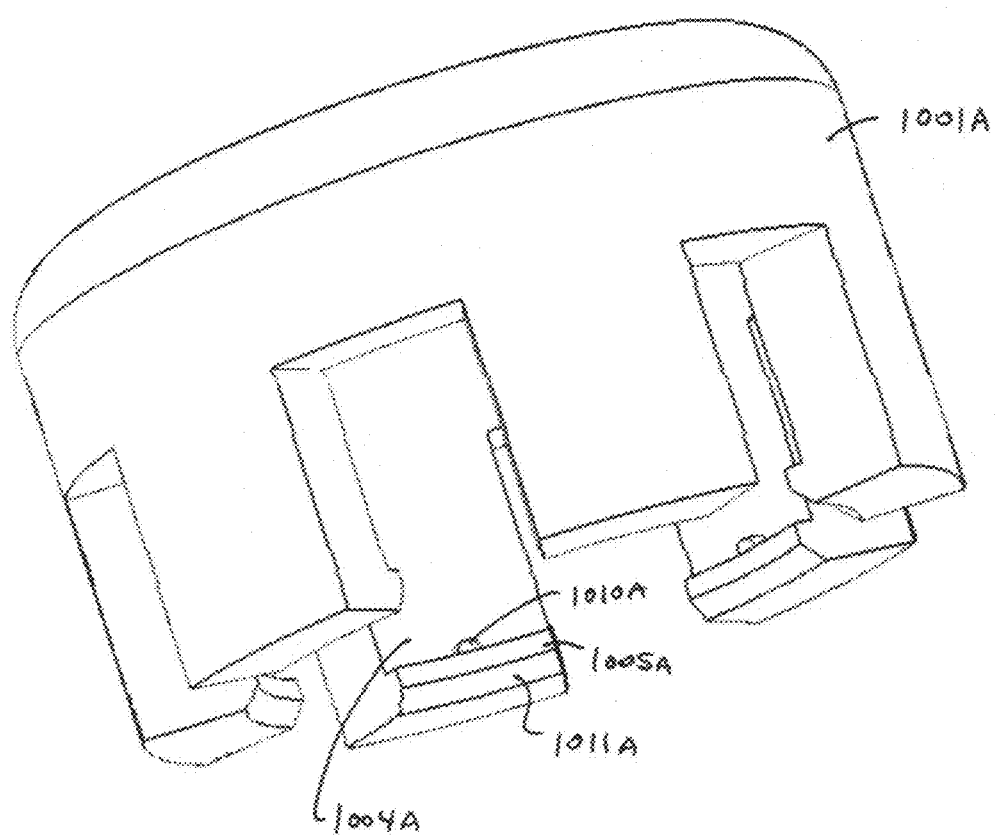
FIG. 10E shows a perspective view of an alternate cap that may be used with the port of FIGS. 10A through 10D.

In one embodiment shown in FIG. 10E, a cap 1001A, may include a detent 1010A in the undercut 1005A of the extension member 1004A. Notably, the undercut 1005A of FIG. 10E includes a sloped portion 1011A to aid in sliding the cap 1001A over the base.

While many ports have a high degree of axial symmetry due to the traditional manufacturing route of machining them on a lathe, newer designs are much more contoured and lack the axial symmetry. The use of snap fits is very advantageous in these designs. These types of designs are much more economically produced using metal injection molding and details that are not economical to machine, such as snap fits, can be added to molded parts without significantly increasing the cost. Sacrificial or soluble cores can be used to add complex detail or undercuts to the injection molded parts. They can also be used to add channels to the bodies of the port to provide for fluid routing or passage.

Figure 12A:
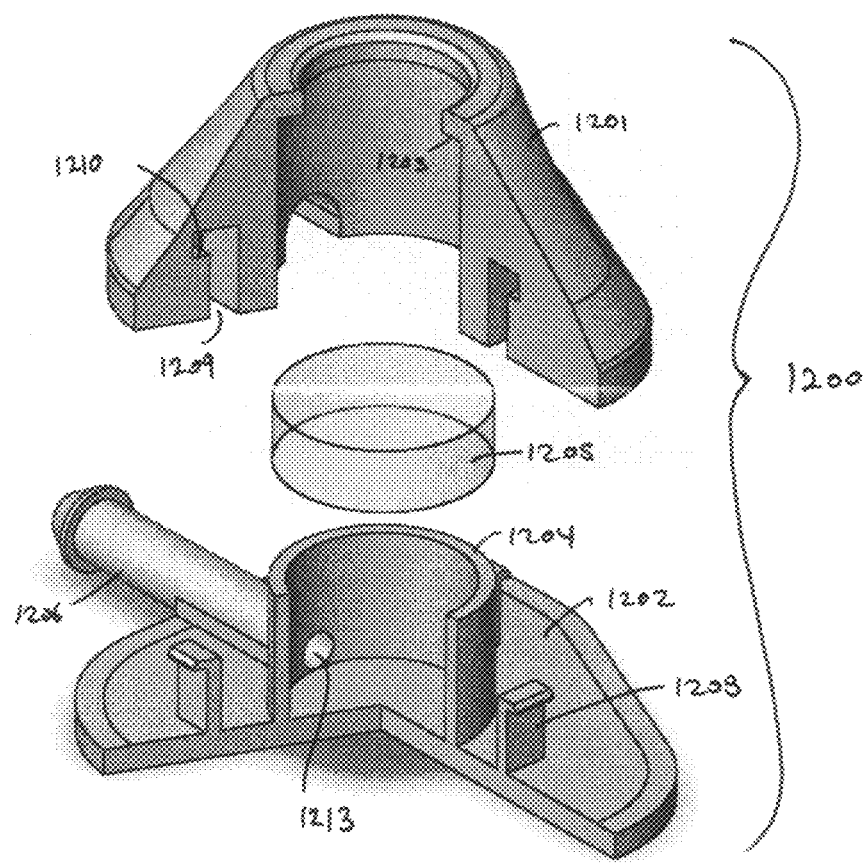
FIGS. 12A through 12C show an assembly sequence of a contoured port with internal snap fit interlock connections.
Figure 12B:
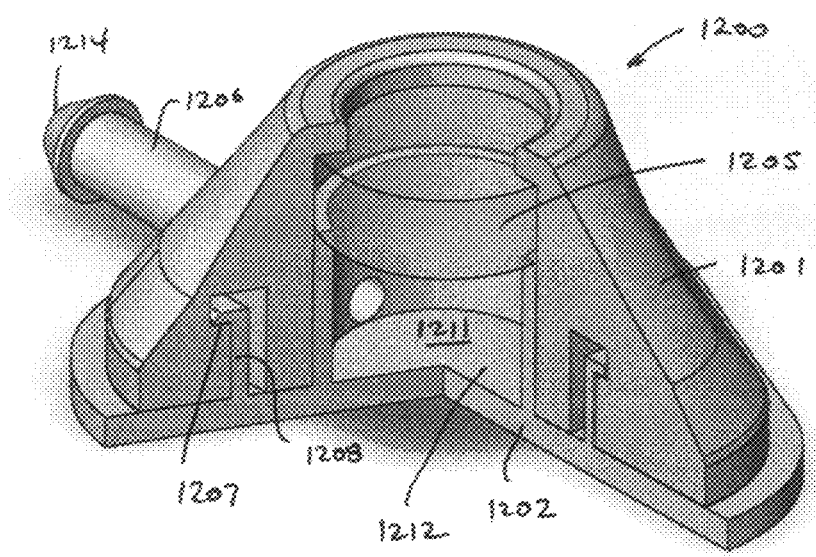
Figure 12C:
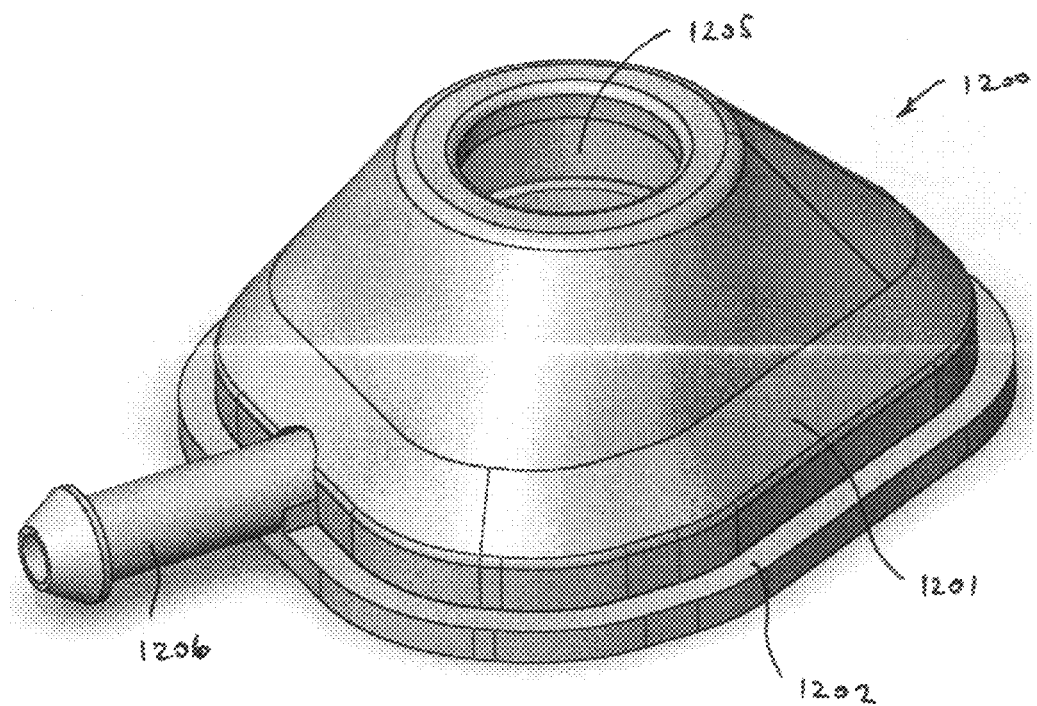

Contoured ports can use snap fit elements extending from the surfaces or details that compress the septum, or can have snap fit elements that are independent of the compression surfaces. FIGS. 12A through 12C depict a contoured port 1200 having internal snap fit elements in the cap 1201 and mating snap fit elements in the base 1202 that that are independent of the compression surface 1203 in the cap and the compression surface 1204 in the base. The compression surfaces 1203, 1204 act on the septum 1205 to secure the septum within the port 1200. This example also includes an integral stem 1206, formed integrally with the base 1202, which helps to reduce the manufacturing cost and the opportunities for leaking. The cap 1201 and base 1202 are pressed together to create an interlock 1207. The fully assembled port 1200 as shown in FIGS. 12B and 12C is securely joined by the snap fit.

Notably, the snap fit elements of port 1200 use a series of linear snap fit extension members 1208 extending from the base 1202. These snap fit elements are formed as cantilevered extension members 1208 that resiliently deflect as the cap 1201 is brought down over them. Once a channel 1209 formed in the cap 1201 clears the extension members 1208, the members return to their natural position and interlock with an undercut 1210 of the cap as shown in FIG. 12B. Once assembled, the port 1200 provides for a reservoir 1211 between the septum 1205 and a floor 1212 of the base 1202. This reservoir 1211 leads to a fluid flow path 1213 extending through the stem 1206 to an outlet 1214.

There are many variations to this approach, for instance the cap may extend past the base to allow the snap fit to temporarily extend past the interlocking surface during assembly, or to create a more aesthetically pleasing assembly.

Another embodiment is a non-symmetric snap fit geometry. This is helpful if port profile has a complicated surface geometry. The snap geometry can follow a complex contour to allow for complete snap while avoiding other features.

Figure 13:
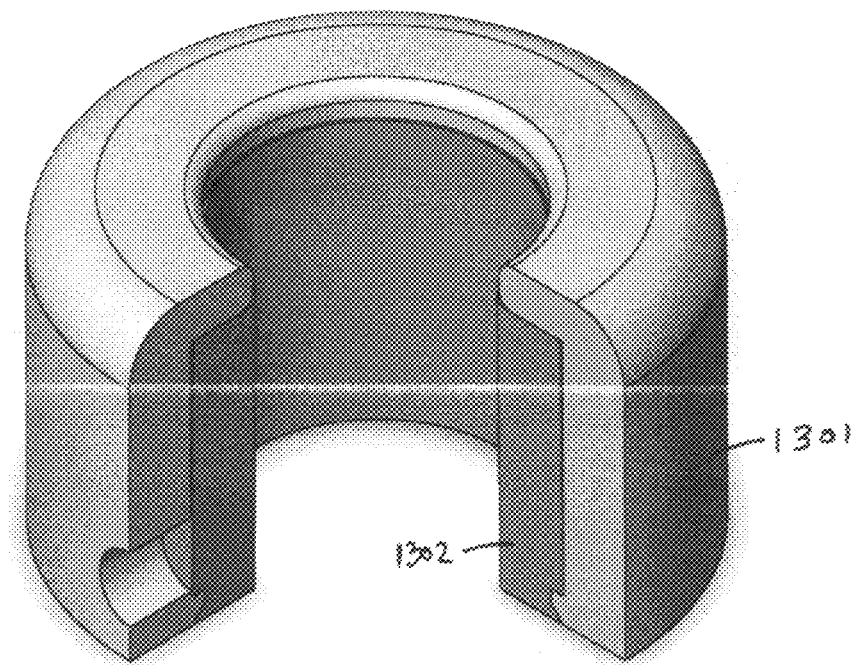
FIG. 13 shows a partial sectional view of a port cap molded around a dissolvable core.
Figure 14:
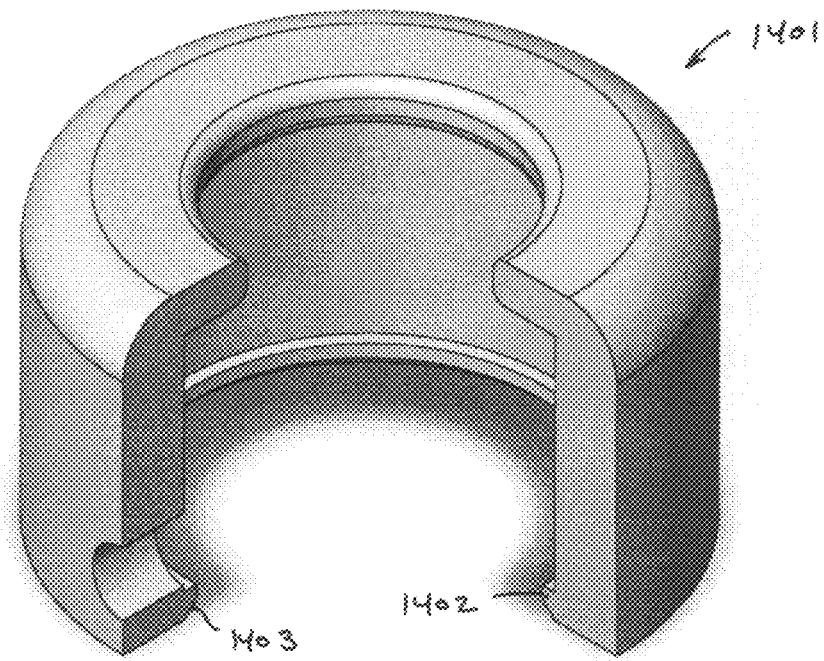
FIG. 14 shows a partial sectional view of the molded port cap of FIG. 13 with the dissolvable core removed.

As previously discussed, metal injection molding is used to fabricate elements that would be difficult or impossible to machine. Undercuts are difficult to mold because the tooling needed to create them is very complex. However molded undercuts can be achieved by using a sacrificial or dissolvable cores during the molding process. FIG. 13 depicts a molded cap having a mold cap body 1301 and a dissolvable core 1302, as an example of how sacrificial or dissolvable cores may be used in the molding process. FIG. 14 shows the cap 1401 after the dissolvable core 1302 has been removed. Here the complex undercut 1402 is clearly shown. Notably, this complex undercut 1402 includes a ramped portion 1403.

The procedure for molding an article with a dissolvable core includes the step of forming a feedstock, typically from titanium powder and thermoplastic binders. This material is then pelletized and molded into the desired shape with the dissolvable core acting as a negative. Once molded, liquid may be used to extract the first phase of the MIM binder prior to thermal debinding. This liquid can be water or a solvent and ideally the dissolvable core material can be chosen to be removed using the same solvent. The article is then debinded before going through a sintering/thermal processing step. This may be the final step in the process although subsequent secondary operation steps, such as hot isostatic pressing, machining, anodizing, polishing, or laser marking may also be added.

Figure 15:
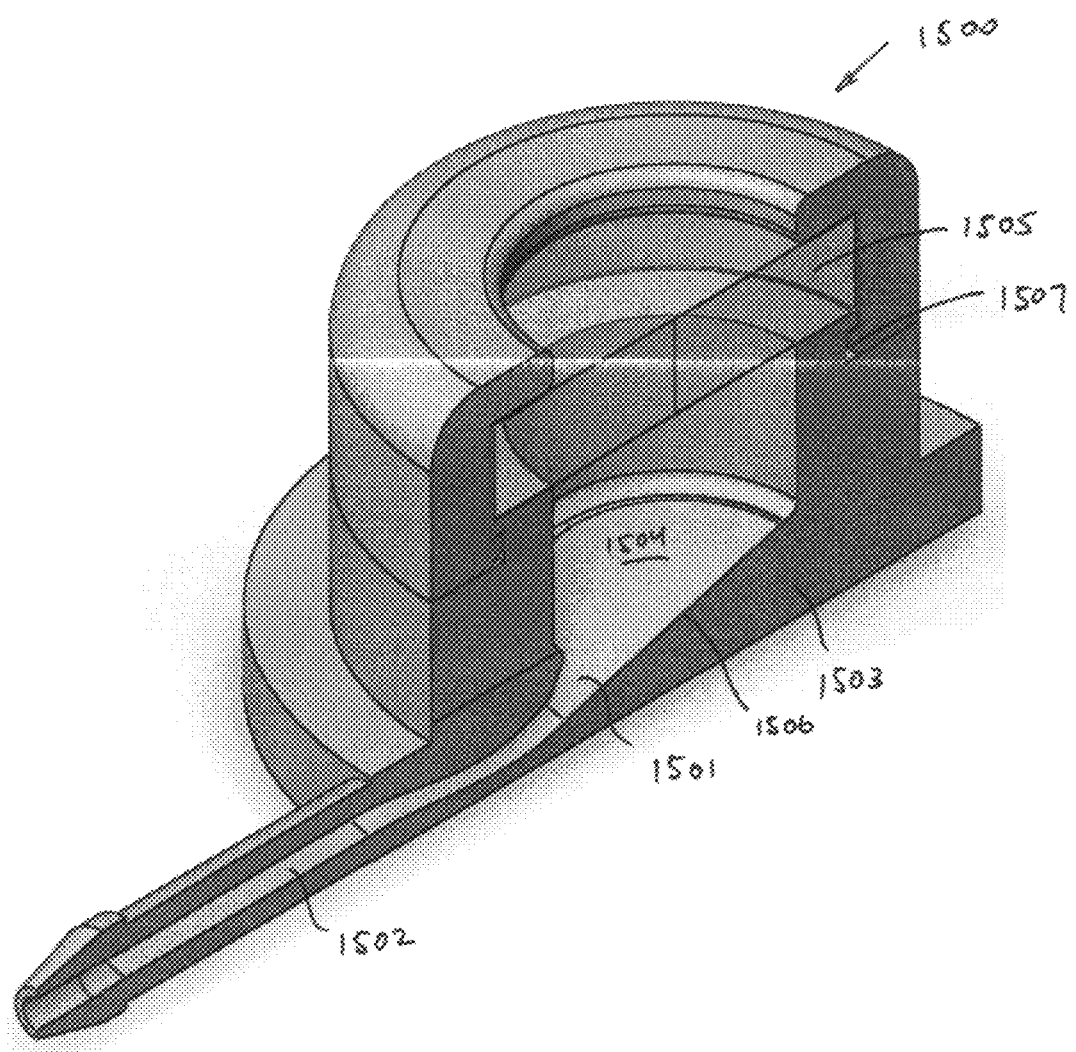
FIG. 15 depicts a cross-section of a port having a sloped funnel-like reservoir exit.

The dissolvable core approach can also be used to form the inner diameter of the stem, complex flow paths within the molded article, or other internal details. One example is the sloped funnel-like feature of FIG. 15. FIG. 15 depicts a cross-section of a port 1500 having a sloped funnel-like exit 1501 and integral stem 1502 created by using a dissolvable core as a negative when molding the base 1503. That is, the reservoir 1504 below the septum 1505 has a sloping floor 1506 which slopes downward toward the integral stem 1502. It is also noted that the port 1500 is shown with a snap fit 1507. However, sloping funnel exits may be formed in ports with more conventional connection features such as press fit connections.

Figure 16:
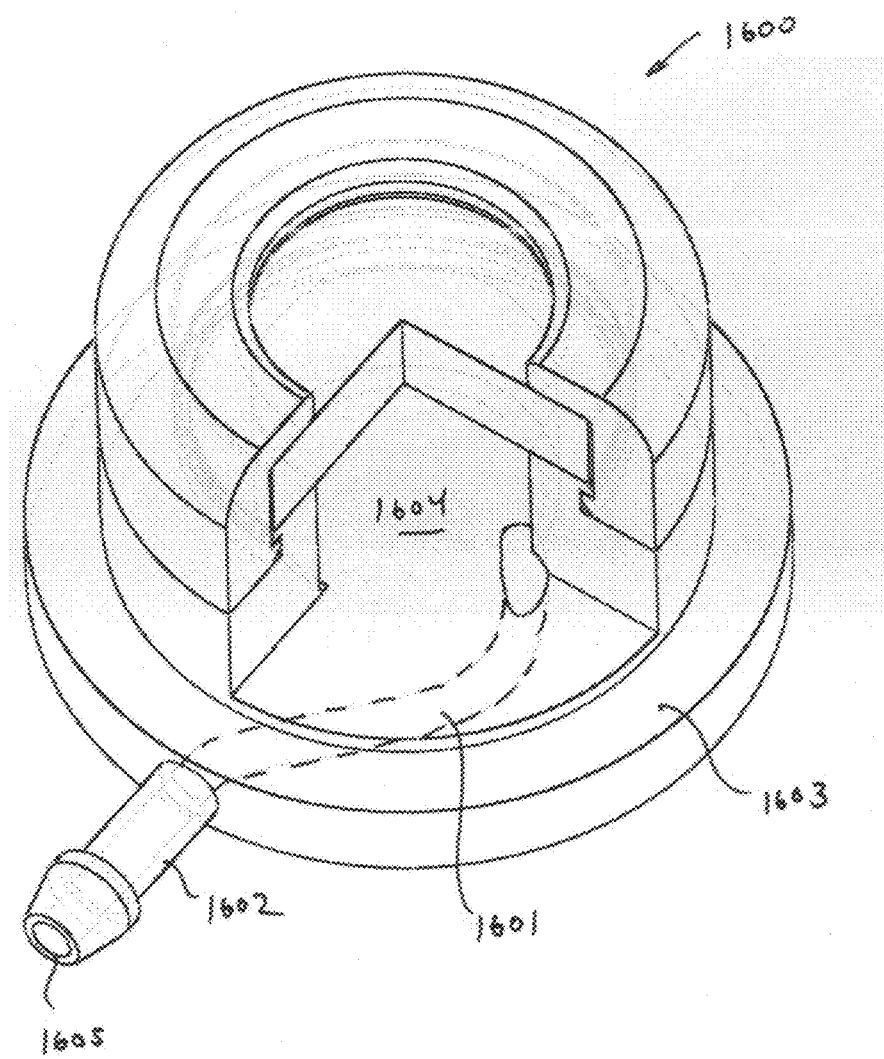
FIG. 16 depicts a partial sectional view of a port having a non-tangential non-radial chamber outlet.

Another example of uses for the dissolvable core approach are complex flow paths such non-tangential non-radial chamber outlet paths. FIG. 16 depicts a partial sectional view of a port 1600 having such a non-tangential non-radial chamber outlet path 1601 and an integral stem 1602 formed using a dissolvable core when molding the base 1603. In this instance, the outlet path 1610 is also non-linear. In other embodiments the outlet path may be linear as well as non-tangential and non-radial. Here, fluid may flow from the reservoir 1604, through the non-tangential non-radial chamber outlet path 1601, into the stem 1602, and finally to the outlet 1605 of the stem. Again, the port 1600 is shown with a snap fit connection but non-tangential non-radial chambers outlets may be provided in more traditionally connected ports, such as those formed with press fits.

Figure 17:
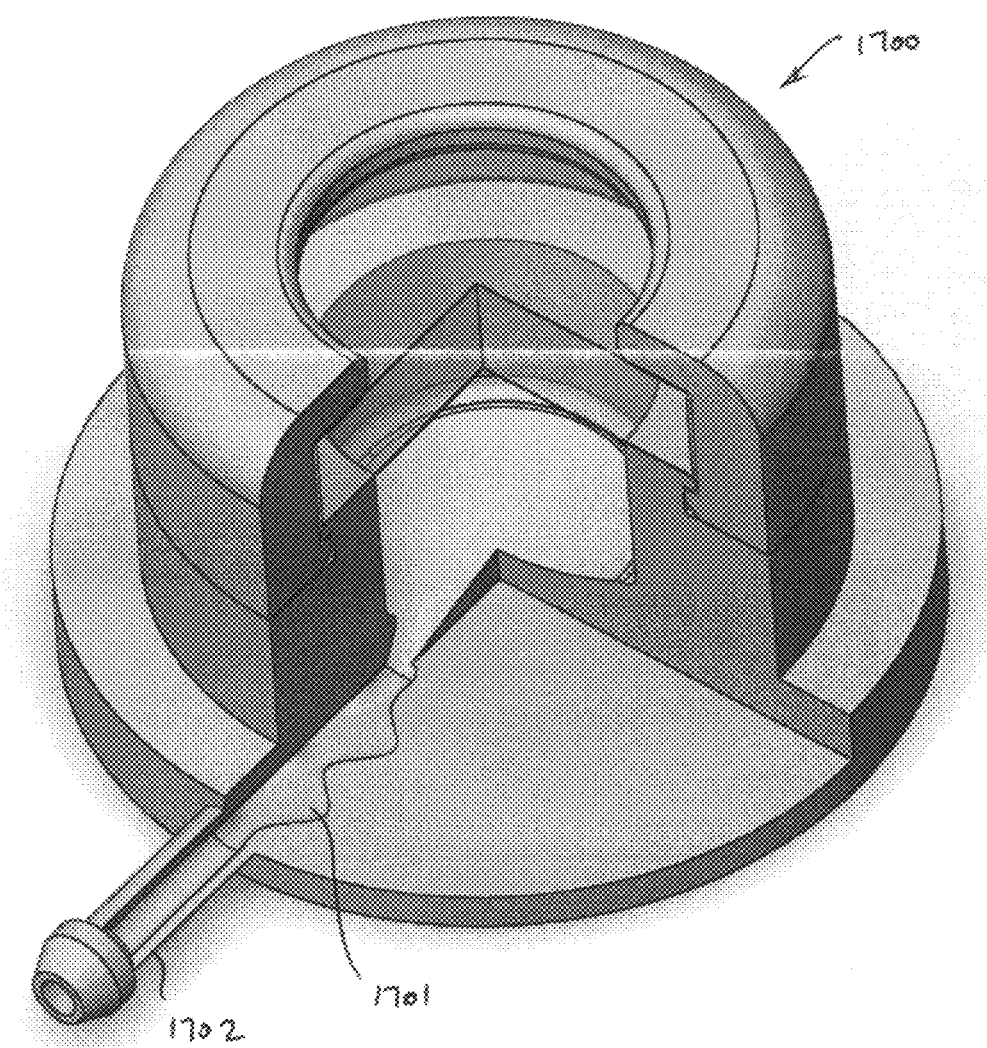
FIG. 17 depicts a partial sectional view of a port having an asymmetric flow path.

Adding turbulence to the flow path of injected liquid can be useful for preventing settling or sticking of fluids and it can also be used to mix fluids. Dissolvable cores can be used to create flow paths that are variable in size to create turbulence or for other purposes. FIG. 17 depicts a partial sectional view of port 1700 having a variable size flow path 1701 and an integral stem 1702 created using a dissolvable core as a negative when molding the base 1703. In this regard, the flow path 1701 has a cross-section that varies its area in different locations along the flow path. Further flow path details can include elements to develop vortices, turbulent flow, or to allow tangential exits in the side of the reservoir. These elements may present themselves as ridges, outcroppings, changes in cross-section or curved surfaces, and can generally be described as textured walls. Port 1700 is shown with snap fit connections. However, it is to be understood that variable size flow paths may be equally provided in conventionally connected ports, such as those with press fit connections.

Dissolvable cores can also be used improve the flow path and design in dual lumen ports. Dual lumen ports have two lumens but are generally desired to have one outlet area, with two catheters attached to the port in close proximity to one another. It is also desirable to have the outlet along the length of the device rather than the width in order to reduce the size of the space needed to implant the device under the skin. Routing both flow channels to a lengthwise end presents design challenges that a dissolvable core can help overcome. In a preferred embodiment of a dual lumen port, a dissolvable core is used to create flow paths in the base of a dual lumen port that exit through the base either along width, or more preferably the length, of the device.

Figure 18:
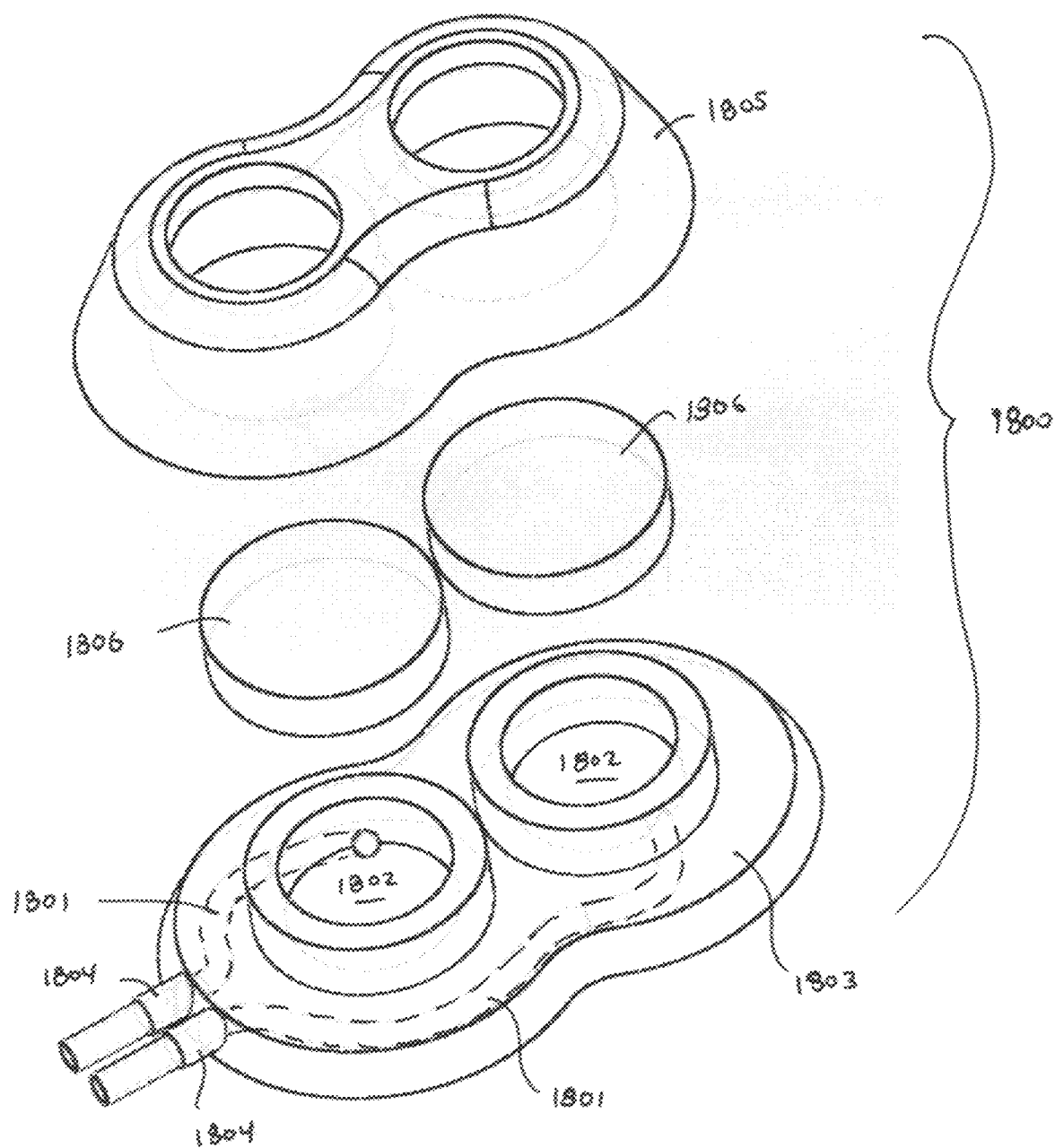
FIG. 18 depicts a dual lumen port with integral flow paths in the base.

FIG. 18 depicts a dual lumen port 1800 with integral flow paths in the base. The flow paths 1801 originate in the reservoirs 1802, proceed through the base 1803, and exit at the stems 1804. The use of a dissolvable core allows these paths to be created without concerns about leaking due to assembly and also formed in a non-tangential non-radial configuration. These paths are also non-linear, although it will be appreciated that the paths may be linear while also being non-tangential and non-radial. Assembly of the cap 1805 and the septa 1806 is completed by use of conventional means or snap fits. Further the exit of the reservoir can be situated on the side wall of reservoir rather than the floor, reducing the ability for the needle to strike the reservoir exit. Dual lumen ports may be configured with snap fit or press fit connections between the cap and base.

While this disclosure primarily addresses situations where both the cap and base of a vascular access port are metal injection molded, it is to be understood that in any of the embodiments one or the other element could be machined, so long as the geometry permits. For example, referring back to the port 600 shown in FIG. 6, it is feasible that the base 603 be machined, e.g. turned on lathe, while the cap 602 is formed through metal injection molding and sacrificial inserts as taught herein. This is due to the relatively simple geometry of the base 603 versus the complex geometry of the cap 602.

Figure 19:
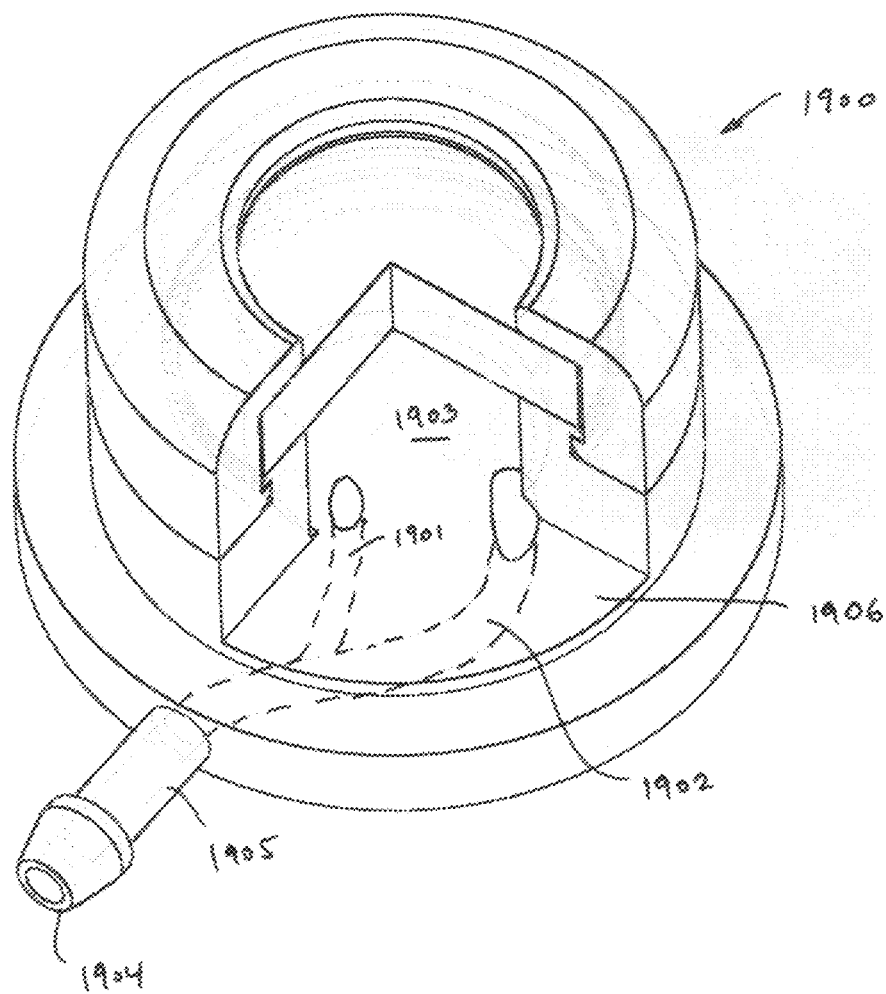
FIG. 19 depicts a partial sectional view of a port having two non-tangential non-radial flow paths merging into a single outlet.

FIG. 19 depicts a partial sectional view of a port 1900 having two non-tangential non-radial flow paths 1901, 1902 emanating from a single reservoir 1903 and subsequently merging within the base 1906 and into a single outlet 1904 of the stem 1905. This configuration may be desirable when, for example, one wishes to control fluid transfer speed through the flow path(s). Again, geometries such as these can be achieved using metal injection molding and sacrificial inserts.

Figure 20:
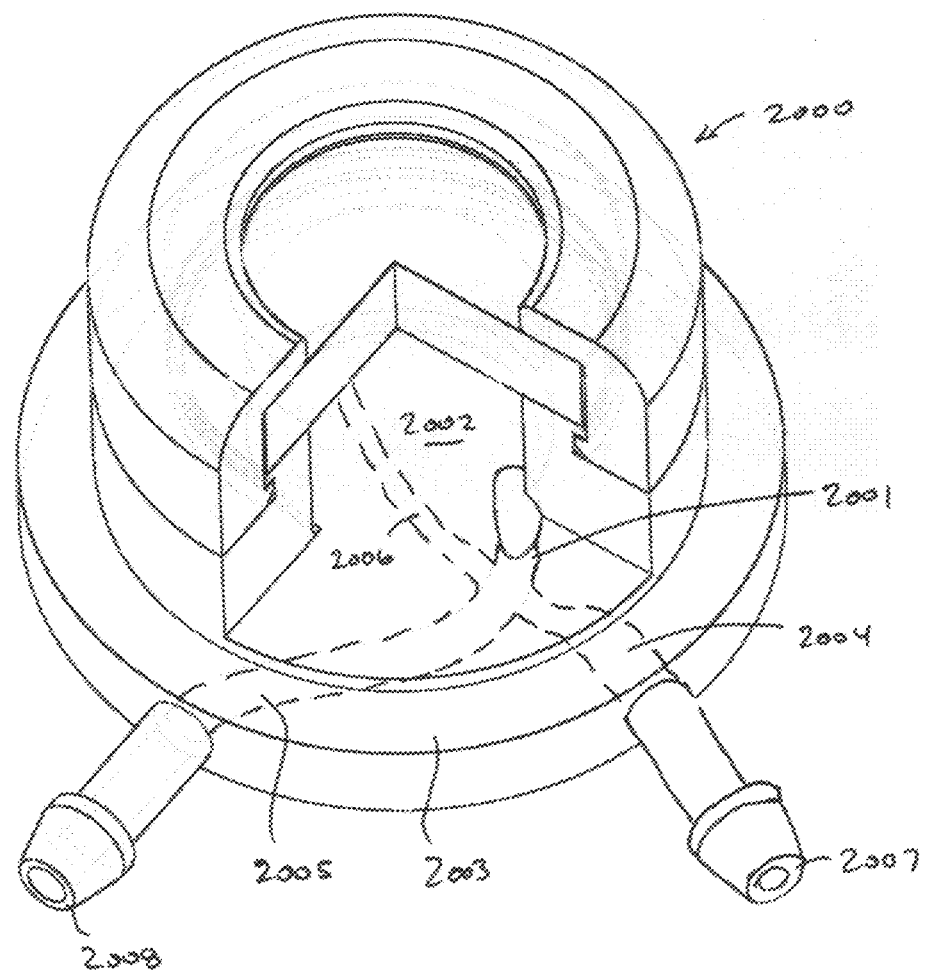
FIG. 20 depicts a partial sectional view of a port having a single non-tangential non-radial flow path splitting internally into multiple non-tangential non-radial flow paths.

FIG. 20 depicts a partial sectional view of a port 2000 having a single non-tangential non-radial flow path 2001 emanating from a reservoir 2002 and subsequently splitting, internal to the base 2003, into multiple non-tangential non-radial flow paths 2004, 2005, 2006 and finally to three separate outlets 2007, 2008 (the third not being shown). This configuration may be desirable when, for example, a caustic liquid is being introduced into the patient and it is desired that the liquid be spread to various vessels within the body rather than concentrated in a single vessel. Again, geometries such as these can be achieved using metal injection molding and sacrificial inserts.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

We claim:

1. A vascular access port adapted to be implanted subcutaneously, said vascular access port comprising:
   a hollow main port structure forming a reservoir above a floor;
   a septum sealing said reservoir in a fluid-tight manner;
   a port outlet, said port outlet including a male projection having an external surface adapted for attachment to a catheter, said port outlet being in fluid communication with said reservoir via a flow path having an internally textured surface separate from said external surface adapted for attachment to a catheter, said internally textured surface causing fluid flowing through said flow path to develop vortices or become turbulent.

2. The vascular access port of claim 1, wherein said main port structure comprises a base and a cap, said flow path being formed in said base through the use of a sacrificial insert.

3. The vascular access port of claim 1, wherein said main port structure comprises a base and a cap, said base and said cap being coupled by at least one linearly engaging snap fit connection.

4. The vascular access port of claim 3, wherein said linearly engaging snap fit connection is engaged by relative linear movement of said cap toward said base, at least one of said base and said cap including a portion which resiliently deflects in a direction perpendicular to said relative linear movement via physical interference to secure said at least one linearly engaging snap fit connection.

5. The vascular access port of claim 1, wherein said main port structure comprises a base and a cap, said base and said cap being coupled by rotational engagement.

6. The vascular access port of claim 1, wherein said floor slopes downward toward said flow path.

7. The vascular access port of claim 1, wherein said flow path is configured to create turbulent flow in fluid flowing from said reservoir to said outlet.

8. The vascular access port of claim 1, wherein said flow path is non-tangential and non-radial.

9. The vascular access port of claim 1, wherein said flow path has a cross-sectional area that varies along its length.

10. A vascular access port adapted to be implanted subcutaneously, said vascular access port comprising:
a base with a floor;
a cap engaged with said base to form a reservoir above said floor;
a septum sealing said reservoir in a fluid-tight manner, said septum having self-sealing properties;
an outlet, said outlet being in fluid communication with said reservoir;
wherein said cap and said base are engaged through rotation of said cap relative to said base; and,
wherein said septum is twisted to impart a torque enhancing the self-sealing properties of the septum.

11. The vascular access port of claim 10, wherein said base and said cap are coupled by at least one snap fit connection.

12. The vascular access port of claim 11, wherein said at least one snap fit connection is engaged by relative movement of said cap and said base, at least one of said base and said cap including portions which resiliently deflect via physical interference to couple said base and said cap.

13. The vascular access port of claim 10, wherein fluid communication between said reservoir and said outlet is through a stem, said stem being adapted to limit rotation of said cap relative to said base.

14. The vascular access port of claim 10, further comprising an asymmetrical fluid flow path between said reservoir and said outlet.

15. A method of providing a vascular access port suitable for subcutaneous implant, said method comprising:
providing a base with a floor;
providing a cap;
fitting a self-sealing septum between the base and the cap and engaging the cap with the base to form a reservoir above the floor, the reservoir being sealed in a fluid-tight manner by the septum;
wherein the engaged cap and base include a fluid flow path from the reservoir to an outlet;
wherein said engaging is achieved through a rotational connection, rotation of the cap relative to the base causing twisting of the septum to improve the self-sealing characteristics of the septum.

16. The method of providing a vascular access port of claim 15, wherein the fluid flow path is asymmetrical.

17. A vascular access port adapted to be implanted subcutaneously, said vascular access port comprising:
a hollow main port structure forming a reservoir above a floor;
a septum sealing said reservoir in a fluid-tight manner;
a port outlet having an external surface adapted to connect to a catheter, said port outlet being in fluid communication with said reservoir via a single flow path having an internal cross-sectional area that varies along its length, the internal flow path being separate from said external surface.

18. The vascular access port of claim 10, wherein said fluid communication is via a flow path having an internally textured wall.

19. The vascular access port of claim 10, wherein said fluid communication is via a flow path having an internal cross-sectional area that varies along its length.

20. The vascular access port of claim 17, wherein said fluid communication is via a flow path having an internally textured wall.

21. The vascular access port of claim 17, wherein said fluid communication is via a flow path having an internal cross-sectional area that varies along its length.

22. The vascular access port of claim 1, wherein said male projection is a separate component apart from said port outlet.

* * * * *